(12) United States Patent
Yamamoto

(10) Patent No.: US 9,474,720 B2
(45) Date of Patent: Oct. 25, 2016

(54) DOSAGE FORM COMPRISING AN ACTIVE INGREDIENT AND A PLURALITY OF SOLID POROUS MICROCARRIERS

(71) Applicant: BioPharmX, Inc., Menlo Park, CA (US)

(72) Inventor: Akira Yamamoto, Cupertino, CA (US)

(73) Assignee: BioPharmX, Inc., Menlo Park, CA (US)

(*) Notice: Subject to any disclaimer, the term of this patent is extended or adjusted under 35 U.S.C. 154(b) by 0 days.

(21) Appl. No.: 14/532,987

(22) Filed: Nov. 4, 2014

(65) Prior Publication Data

US 2015/0125496 A1 May 7, 2015

Related U.S. Application Data

(60) Provisional application No. 61/899,298, filed on Nov. 4, 2013, provisional application No. 61/973,270, filed on Apr. 1, 2014.

(51) Int. Cl.

| *A61K 31/65* | (2006.01) |
|---|---|
| *A61K 31/14* | (2006.01) |
| *A61K 31/375* | (2006.01) |
| *A61K 31/519* | (2006.01) |
| *A61K 47/02* | (2006.01) |
| *A61K 9/50* | (2006.01) |
| *A61K 9/00* | (2006.01) |
| *A61K 47/34* | (2006.01) |
| *A61K 47/44* | (2006.01) |
| *A61K 9/16* | (2006.01) |

(52) U.S. Cl.
CPC .......... *A61K 9/5015* (2013.01); *A61K 9/0014* (2013.01); *A61K 9/1611* (2013.01); *A61K 9/5026* (2013.01); *A61K 9/5089* (2013.01); *A61K 31/14* (2013.01); *A61K 31/375* (2013.01); *A61K 31/519* (2013.01); *A61K 31/65* (2013.01); *A61K 47/02* (2013.01); *A61K 47/34* (2013.01); *A61K 47/44* (2013.01)

(58) Field of Classification Search
CPC .... A61K 47/02; A61K 31/14; A61K 31/519; A61K 31/65; A61K 31/375
See application file for complete search history.

(56) References Cited

U.S. PATENT DOCUMENTS

| 4,690,825 A | 9/1987 | Won |
| 4,873,091 A | 10/1989 | Jankower et al. |
| 4,962,133 A | 10/1990 | Chromecek et al. |
| 4,962,170 A | 10/1990 | Chromecek et al. |
| 5,145,675 A | 9/1992 | Won |
| 5,200,236 A | 4/1993 | Lang et al. |
| 5,550,044 A | 8/1996 | Kosak et al. |
| 5,834,577 A | 11/1998 | Sojka |
| 5,879,716 A | 3/1999 | Katz et al. |
| 5,955,109 A | 9/1999 | Won et al. |
| 6,248,849 B1 | 6/2001 | Sojka |
| 6,462,025 B2 | 10/2002 | Vishnupad |
| 6,685,966 B1 | 2/2004 | Dominique et al. |
| 6,958,148 B1* | 10/2005 | Green .............. A61K 8/11 424/401 |
| 7,476,694 B2 | 1/2009 | Baran, Jr. et al. |
| 7,537,803 B2 | 5/2009 | Wang et al. |
| 7,541,347 B2 | 6/2009 | Wortzman et al. |
| 8,343,945 B2 | 1/2013 | Tamarkin et al. |
| 8,357,318 B2 | 1/2013 | Guisinger et al. |
| 8,435,474 B2 | 5/2013 | Fomitchev et al. |
| 2003/0134100 A1 | 7/2003 | Mao et al. |
| 2004/0157766 A1* | 8/2004 | Embil et al. .............. 514/1 |
| 2004/0242729 A1 | 12/2004 | Baran, Jr. et al. |
| 2006/0167147 A1 | 7/2006 | Asgari |
| 2008/0070140 A1 | 3/2008 | Fomitchev et al. |
| 2008/0268062 A1 | 10/2008 | Baran et al. |
| 2008/0299046 A1 | 12/2008 | White et al. |
| 2009/0274765 A1 | 11/2009 | Beduneau et al. |
| 2011/0027172 A1 | 2/2011 | Wang et al. |
| 2011/0039947 A1 | 2/2011 | Sharma et al. |
| 2011/0212157 A1 | 9/2011 | Edelson et al. |

(Continued)

FOREIGN PATENT DOCUMENTS

| EP | 0306236 B1 | 4/1993 |
| EP | 0510761 B1 | 3/1995 |
| EP | 0436971 B1 | 12/1997 |
| WO | WO 03/016410 A2 | 2/2003 |

(Continued)

OTHER PUBLICATIONS

Notification of Transmittal of International Search Report and Written Opinion of the International Searching Authority, or the Declaration for PCT application PCT/US2014/063942, dated Feb. 5, 2015.

*Primary Examiner* — Alma Pipic
(74) *Attorney, Agent, or Firm* — Robert Kehl Sink; Susan T. Evans; McDermott Will & Emery LLP

(57) ABSTRACT

The present application provides a dosage form and related methods for making the dosage form. The dosage form generally comprises a hydrophilic active ingredient, a plurality of solid, porous microcarriers, each having a hydrophobic surface, an optional hydrophobic encapsulant, and a hydrophilic delivery agent, wherein (i) the hydrophilic active ingredient is associated with the plurality of solid, porous microcarriers, (ii) the plurality of solid, porous microcarriers is encapsulated by the hydrophobic encapsulant, and (iii) the hydrophilic delivery agent is physically separated from a majority of the hydrophilic active ingredient by a boundary between the hydrophilic delivery agent and the hydrophobic encapsulant. In some embodiments, the dosage form is for topical application. In some additional embodiments, the plurality of solid, porous microcarriers is formed by modifying the microcarriers to increase their hydrophobicity.

20 Claims, 7 Drawing Sheets

(56) References Cited

U.S. PATENT DOCUMENTS

| | | |
|---|---|---|
| 2012/0039824 A1 | 2/2012 | Archer et al. |
| 2012/0219728 A1 | 8/2012 | Badri et al. |
| 2012/0328701 A1 | 12/2012 | Edelson et al. |
| 2013/0064777 A1 | 3/2013 | Tamarkin et al. |

FOREIGN PATENT DOCUMENTS

| | | |
|---|---|---|
| WO | WO 2009/087633 A2 | 7/2009 |
| WO | WO 2012/047098 A1 | 4/2012 |
| WO | WO 2012/100097 A2 | 7/2012 |
| WO | WO 2013/056132 A2 | 4/2013 |

* cited by examiner

DOSAGE FORM COMPRISING AN ACTIVE INGREDIENT AND A PLURALITY OF SOLID POROUS MICROCARRIERS

CROSS-REFERENCE TO RELATED APPLICATIONS

This application claims the benefit of priority to U.S. Provisional Application No. 61/899,298 filed Nov. 4, 2013 and to U.S. Provisional Application No. 61/973,270 filed Apr. 1, 2014, the contents each of which is incorporated herein by reference in its entirety.

FIELD

This disclosure relates generally to a dosage form for delivery of an active ingredient to a patient. More particularly, this disclosure is directed to a dosage form comprising an active ingredient associated with a plurality of solid porous microcarriers in a hydrophobic encapsulant, dispersed within a hydrophilic delivery agent. Also provided are methods for fabricating the aforementioned dosage form.

BACKGROUND

Many active compounds are sensitive to degradation by contact with hydrophilic oxidizing or reducing agents and/or water (collectively, referred to herein as reactive hydrophilic agents). However, many active ingredients are advantageously delivered in hydrophilic vehicles, oftentimes making delivery of compounds that are sensitive to interaction with reactive hydrophilic agents a challenge. For example, for topically applied medicines, many consumers prefer hydrophilic creams and lotions to hydrophobic oils and ointments. Moreover, absorption and transcutaneous delivery of many active ingredients is often facilitated by the use of a hydrophilic delivery agent.

One method to keep an active compound separated from a reactive hydrophilic agent is to physically encapsulate the active ingredient to limit its interaction/exposure to the reactive hydrophilic agent. Physical encapsulation can be achieved by a wide variety of techniques. For example, physical encapsulation can be achieved using liposomes, emulsions, microcarriers, nanocarriers, and the like.

When protecting active ingredients that (1) are strongly hydrophobic and (2) do not have polar or ionic functional groups, the methods of encapsulation are relatively straightforward. For example, the hydrophobic active ingredient can be mixed with a dispersed phase comprising a hydrophobic encapsulant, a continuous phase comprising a hydrophilic delivery agent, and an emulsifier (e.g., a surfactant). This combination can be used to form an oil-in-water type emulsion that can effectively limit the interaction between the hydrophobic active ingredient and reactive hydrophilic agents.

On the other hand, some active ingredients are hydrophilic (or slightly hydrophobic) or have polar or ionic functional groups. Such active ingredients can be more difficult to protect with simple oil-in-water type emulsions if they are drawn to interact with the hydrophilic phase of the emulsion, thus exposing such ingredients to reactions with reactive hydrophilic agents.

Other methods have been developed to protect such molecules. For example, water-in-oil-in-water type emulsions can be formed in which the active ingredient is isolated inside of an oil phase to first form a water-in-oil emulsion, prior to a second step of mixing with a hydrophilic vehicle. Such water-in-oil-in-water emulsions can be difficult to fabricate, require multiple steps, and can be unstable when deployed commercially, where vendors, consumers, and regulatory agencies typically require data demonstrating multiple years of stability for the active ingredient. Additionally, many active ingredients that are hydrophilic are immiscible with the hydrophobic dispersed phase of an emulsion, which makes it difficult to introduce the active ingredient into the emulsion.

Some emulsions suffer from low encapsulation efficiency in which only a small portion, in some cases less than half, of the active ingredient is encapsulated within the dispersed phase, while the remainder of the active ingredient is mixed into the hydrophilic continuous phase of the emulsion. Low encapsulation efficiency can lead to degradation of a large portion of the active ingredient when hydrophilic reactive agents are introduced into the continuous phase of the emulsion, and can also lead to a non-uniform drug environment, which is undesirable from both a manufacturing and administration standpoint.

Another method that has been developed is microencapsulation. In this process, the active ingredient is reduced in size, or micronized, and coated with a coating material. The coated active ingredient particles are then mixed into a hydrophilic delivery agent, where the coating protects the active ingredient from interaction with one or more reactive hydrophilic agents that may be present. This microencapsulation technique also has associated drawbacks. For example, coating efficiency can be poor in such processes and the solid particles comprising the active ingredient can separate from the hydrophobic dispersed phase due to poor surface affinity or wettability. Techniques such as dispersion via emulsification in a liquid phase or spray drying in a gas phase have been developed to circumvent these challenges, but such approaches can be cumbersome, expensive, time-consuming, and difficult to control.

Therefore, there is a need for a dosage form that protects an active ingredient from reactive hydrophilic agents when the active ingredient is hydrophilic, or is slightly hydrophobic, or has polar or ionic functional groups. Reactive hydrophilic agents can include, for example, hydrophilic oxidizing agents, hydrophilic reducing agents, and water. The dosage form should maintain a high degree of potency, i.e., activity, of the active ingredient, provide efficient encapsulation of the active ingredient, and limit interaction of the active ingredient with a hydrophilic delivery agent until its application to the target surface, tissue, or organ.

BRIEF SUMMARY

The present disclosure overcomes the limitations of the prior art by providing, in one aspect, a dosage form that comprises (i) a hydrophilic active ingredient, (ii) a plurality of solid, porous microcarriers, each having a hydrophobic surface, (iii) an optional hydrophobic encapsulant, and (iv) a hydrophilic delivery agent.

Thus, in one or more embodiments, provided is a dosage form that comprises a hydrophilic active ingredient, a plurality of solid, porous microcarriers, each having a hydrophobic surface, and a hydrophilic delivery agent in which the plurality of solid, porous microcarriers and hydrophilic active ingredient are comprised.

In one or more further embodiments, provided is a dosage form that comprises a hydrophilic active ingredient, a plurality of solid, porous microcarriers, each with a hydrophobic surface, a hydrophobic encapsulant, and a hydrophilic delivery agent in which the plurality of solid, porous microcarriers, hydrophilic active ingredient, and hydrophobic encapsulant are comprised.

In one or more embodiments, the hydrophilic active ingredient and the plurality of solid, porous microcarriers are encapsulated by the hydrophobic encapsulant.

In one or more additional embodiments related to one or more of the foregoing, the hydrophilic active ingredient is associated with the plurality of solid, porous microcarriers, each having a hydrophobic surface.

In one or more preferred embodiments of the dosage form, the active ingredient that is associated with the plurality of porous microcarriers is partitioned from the hydrophilic delivery agent by a phase boundary between the hydrophobic encapsulating agent and the hydrophilic delivery agent.

In one or more additional embodiments, the dosage form comprises, on the outer surface of the encapsulated plurality of porous microcarriers associated with the active ingredient, an overcoat layer.

In one or more embodiments, the Log D value of each solid, porous microcarrier is higher than the Log D value of the hydrophobic encapsulant. In any one or more of the embodiments described herein, the plurality of solid, porous microcarriers each comprise a hydrophobically-modified surface.

In one or more embodiments, one or more microcarriers in the plurality of solid, porous microcarriers has a minimum cross-sectional dimension in the range of about 1 micrometer to about 200 micrometers, e.g. from about 1 micrometers to about 100 micrometers or from about 5 micrometers to about 50 micrometers.

In one or more additional embodiments, microcarriers may comprise microspheres or microtubules.

In one or more embodiments, the dosage form is a solid.

In one or more alternative embodiments, the dosage form is a liquid.

In one or more embodiments, the active ingredient is homogenously distributed within the dosage form.

In one or more additional embodiments, the plurality of solid, porous microcarriers comprises a material selected from the group consisting of hydrophobic surface-modified silicon dioxide, porous polystyrene, porous polyamide, porous hydrophobic cellulose, and porous polytetrafluoroethylene.

In one or more further embodiments, the microcarrier possesses a porous structure for retaining the active ingredient, a hydrophobic outer surface, a particle size of 1 nanometer to 100 micrometers, and is chemically non-reactive with the active ingredient.

In yet one or more additional embodiments, the hydrophobic encapsulant comprises a material selected from the group consisting of mineral oil, petrolatum jelly, synthetic waxes, natural waxes, and silicone oils.

In one or more embodiments, the hydrophilic delivery agent comprises a material selected from the group consisting of propylene glycol, polyethylene glycol, and glycerin.

In one or more embodiments, the hydrophilic delivery agent possesses a viscosity effective for suspension of the encapsulated hydrophobic microcarriers therein.

In one or more embodiments, the hydrophilic delivery agent is effective to dissolve the active ingredient. This dissolution, may in certain embodiments, assist with delivery of the active agent to a target location or target tissue.

In one or more embodiments, the silane coupling agent comprises a material selected from the group comprising trimethoxy(octadecyl)silane, octadecyltrichlorosilane, and octyldimethylchlorosilane. In one or more embodiments, desired characteristics for the silane coupling agent include having a contact angle of larger than 100 degrees when placed in contact with water and ability to attach to the surface of a microcarrier to make the surface of the microcarrier hydrophobic.

In one or more embodiments, the solvent for the silane coupling agent comprises a material selected from the group comprising toluene, heptane, and octane.

In one or more embodiments, the dosage form is a topical formulation, i.e., for topical application, e.g., to human skin.

In one or more embodiments, the dosage form is for corneal or mucosal delivery.

In one or more embodiments, the dosage form is delivered orally as a liquid or gel cap.

In one or more embodiments, the dosage form is delivered orally as a solid, such as a tablet.

In one or more embodiments, the active ingredient comprised within the dosage form is a small molecule.

In one or more additional embodiments, the small molecule is an antibiotic and/or an antifungal agent. In one or more further embodiments, the active ingredient comprises a small molecule drug selected from the group consisting of erythromycin, itraconazole, and ketoconazole.

In yet one or more additional embodiments, the active ingredient comprises a tetracycline-class antibiotic. In one or more preferred embodiments, the active ingredient is minocycline. In one or more preferred embodiments, the active ingredient comprises minocycline and the dosage form is for topical application to the skin, for example, for the treatment of acne.

In yet one or more additional embodiments, the active ingredient is a dietary supplement. Examples of such active ingredients include L-methylfolate, vitamin C, and choline hydroxide, among others.

In one or more embodiments, the active ingredient is classified as a cosmetic ingredient by the U.S. Food and Drug Administration. Examples of cosmetic active ingredients vitamin C, tocopherol, and sodium hyaluronate, among others.

In yet a further aspect, provided is a dosage form that comprises a hydrophilic active ingredient, a plurality of solid, porous microcarriers, each having a hydrophobic surface, where the active ingredient is associated with the plurality of solid, porous microcarriers, and a hydrophobic encapsulant, wherein the active ingredient in association with the plurality of solid, porous microcarriers is encapsulated by the hydrophobic encapsulant.

In another aspect, provided is a method for preparing a dosage form as described herein. For example, the dosage form is prepared by the following steps: (i) providing a plurality of hydrophobic microcarriers, (ii) dissolving an active ingredient as provided herein in a solvent to form a first solution, (iii) mixing the plurality of hydrophobic microcarriers with the first solution to form a first mixture, (iv) removing at least a majority of the solvent from the first mixture using, e.g., heat or vacuum to form a second mixture, and (v) mixing the second mixture with a hydrophilic delivery agent and, optionally, with a hydrophobic encapsulant to form the dosage form.

In one or more embodiments, the method comprises incorporating a hydrophobic encapsulant in step (v), where the encapsulant and the delivery agent are added and mixed either simultaneously or in a stepwise fashion.

In one or more embodiments related to the method, the second mixture is mixed with the hydrophobic encapsulant to form a third mixture prior to mixing the third mixture with the hydrophilic delivery agent.

In yet one or more further embodiments, the final dosage form is prepared absent the addition and mixing of a hydrophilic delivery agent.

In an exemplary method, the plurality of hydrophobic microcarriers is prepared by mixing a hydrophilic, solid, porous microcarrier, a silane-coupling agent, and a (optional) solvent for the silane-coupling agent to form a mixture, and heating the mixture to effect coupling of the silane coupling agent to the surface of the hydrophilic, solid porous microcarrier. The resulting product, i.e., a plurality of hydrophobic microcarriers, comprises a plurality of hydrophobically-modified microcarriers. In one or more embodiments, the heating step is performed under low pressure (i.e., at a pressure at or less than about 0.2 atm, e.g., from about 0.03 atm to about 0.2 atm) or under medium to high vacuum (e.g., from about $1 \times 10^{-9}$ Torr to about 25 Torr) to enhance the rate of removal of solvent. In one or more embodiments, the heating step is performed gradually (i.e., over a period of 10 minutes to 26 hours) to allow sufficient time for the silane-coupling agent to interact with the surface of the microcarriers.

Additional embodiments of the dosage form, related methods, components of the dosage form, and the like will be apparent from the following description, examples, figures and claims. These and other objects and features of the disclosure will become more fully apparent when read in conjunction with the following detailed description.

BRIEF DESCRIPTION OF THE DRAWINGS

FIGS. 1A, 1B, 1C, and 1E were captured using illumination with a standard white filament bulb (white light illumination). FIGS. 1D and 1F are the same portion of the dosage form as shown in FIGS. 1C and 1E, respectively, under illumination with an ultraviolet (UV) light source to capture fluorescence of the active ingredient, minocycline.

DETAILED DESCRIPTION

Figure 1A:
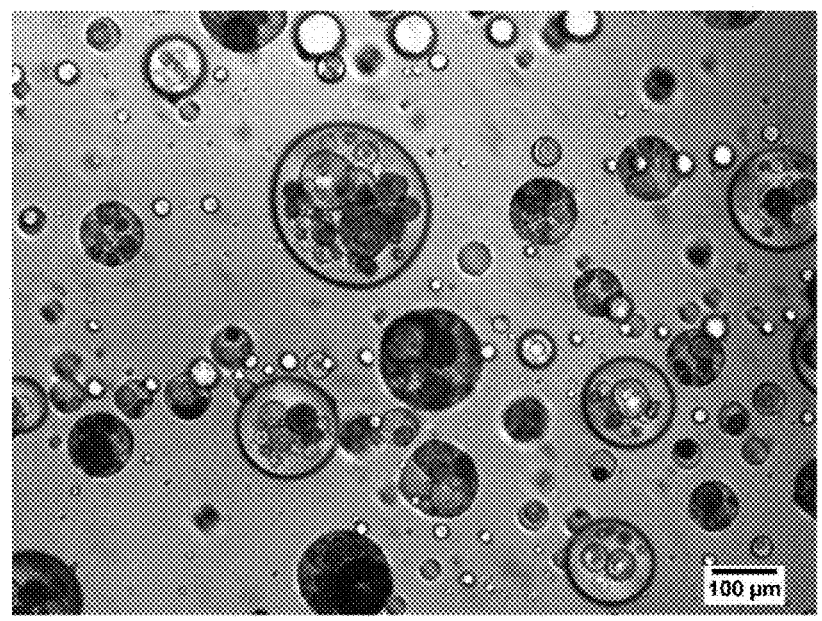
FIGS. 1A-1F are microscope images of an exemplary dosage form produced as described in Example 1.
Figure 1B:
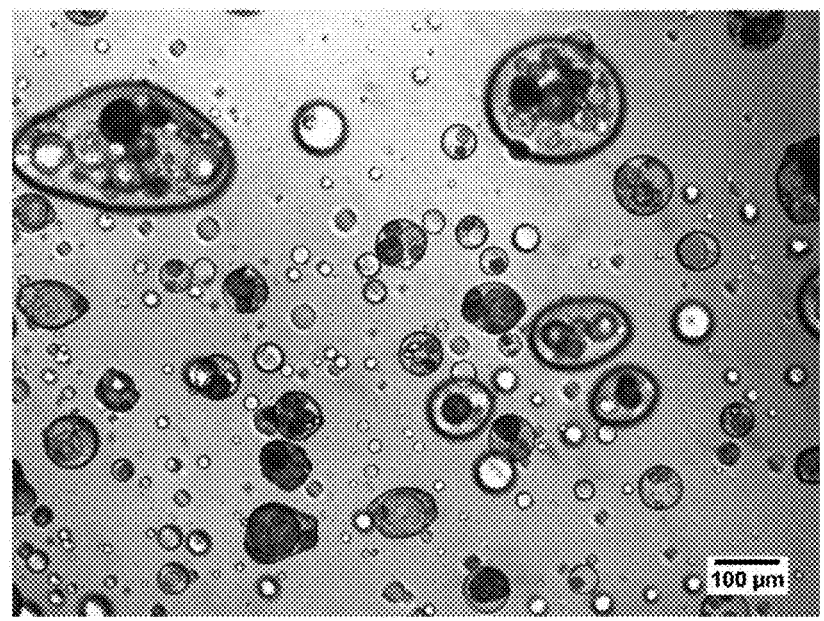
Figure 1C:
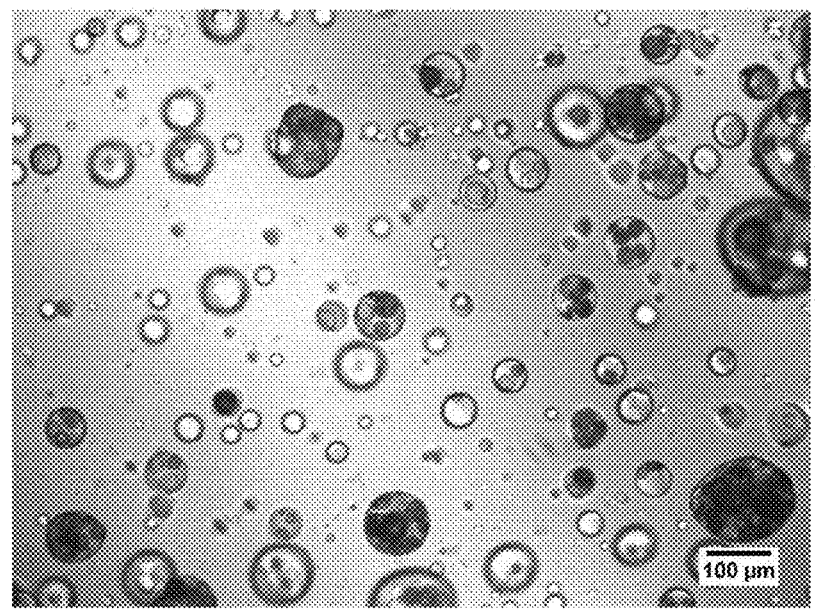
Figure 1D:
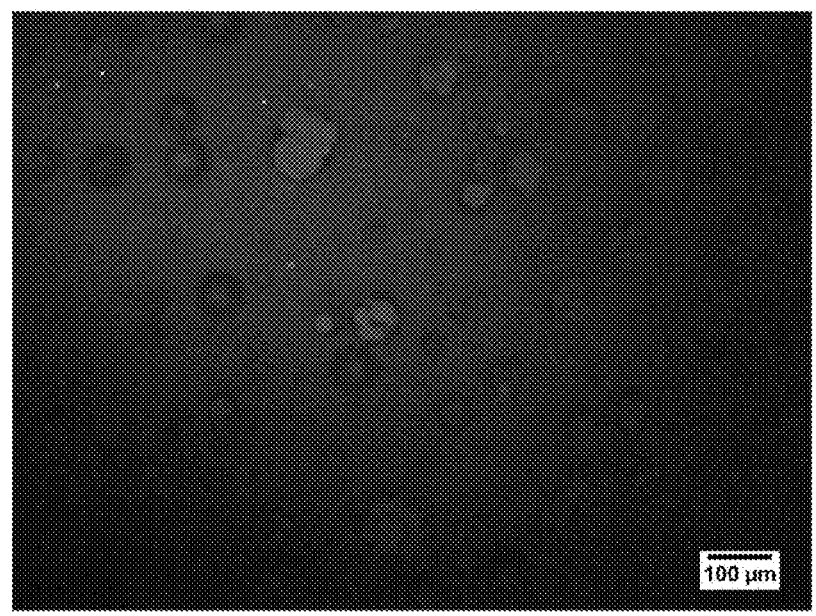
Figure 1E:
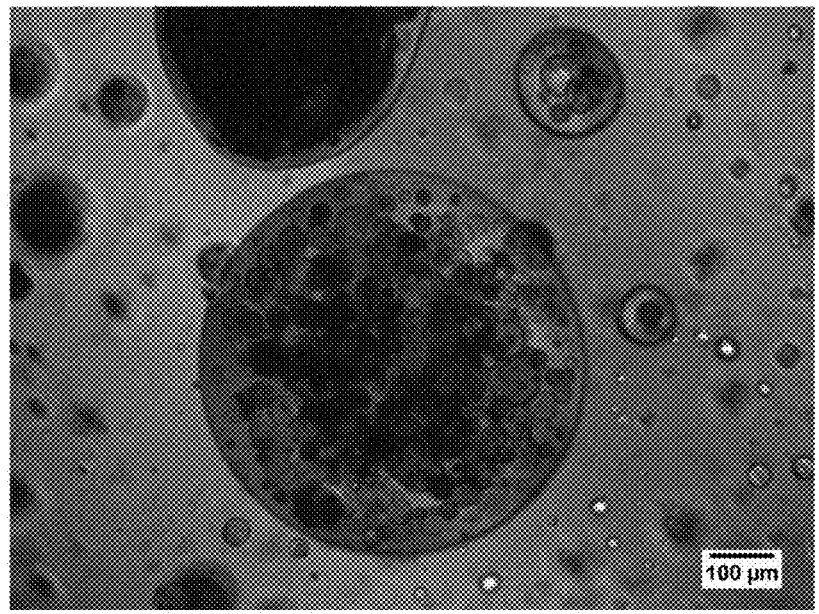
Figure 1F:
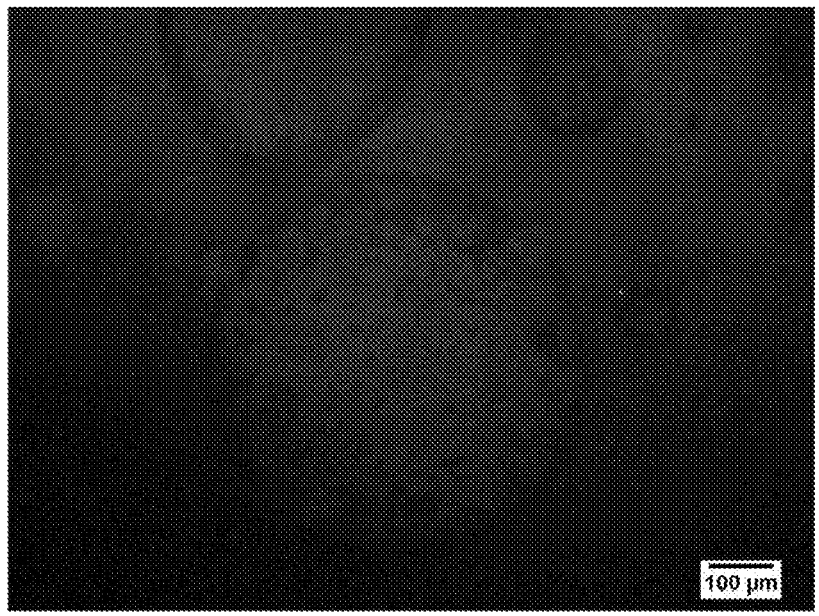
Figure 2:
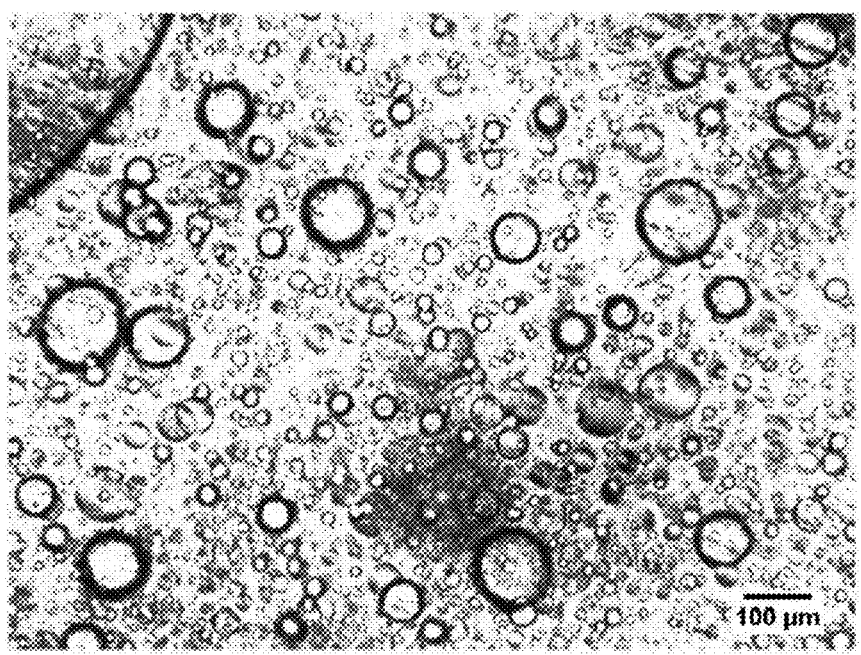
FIG. 2 is a microscope image of a dosage form comprising non-surface-modified, hydrophilic microcarriers and an antibiotic prepared as described in Example 2. The image was captured under white light illumination.
Figure 3A:
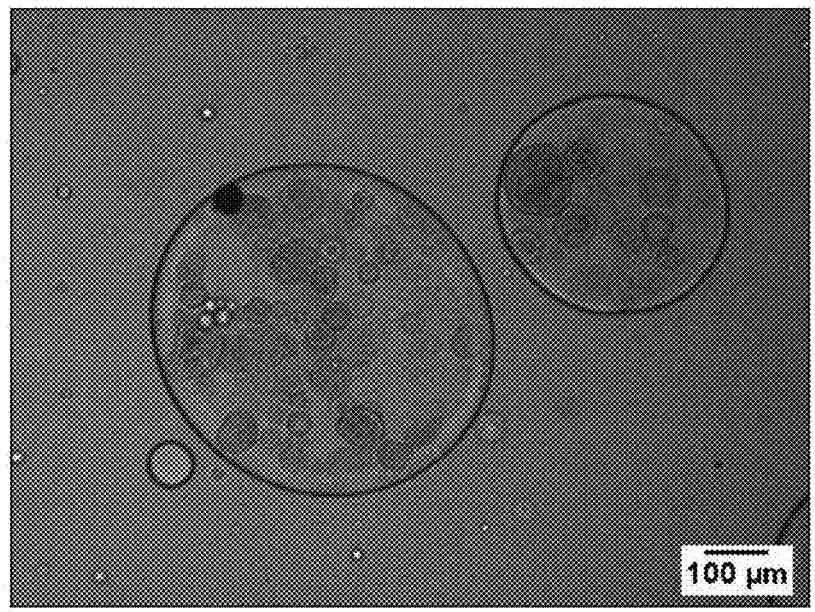
FIGS. 3A and 3B are microscope images of an exemplary dosage form produced as described in Example 3. The image in FIG. 3A was captured under white light illumination. The image in FIG. 3B illustrates fluorescence from the illustrative active ingredient, minocycline, stabilized with magnesium, when illuminated under UV light.
Figure 3B:
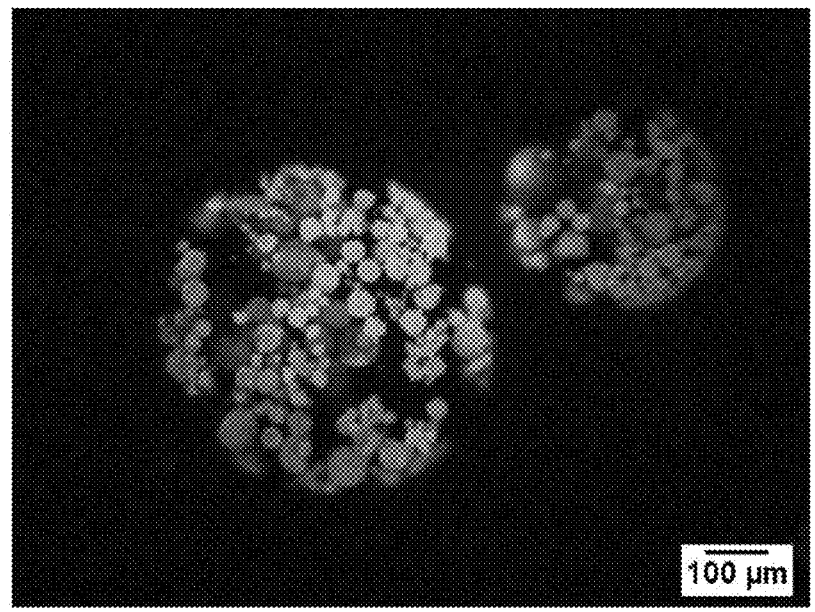

The present invention will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document which are incorporated herein by reference.

Definitions

It must be noted that, as used in this specification, the singular forms "a," "an," and "the" include plural referents unless the context clearly dictates otherwise. Thus, for example, reference to an "active ingredient" includes a single ingredient as well as two or more different ingredients, reference to a "microcarrier" refers to a single microcarrier as well as to two or more different microcarriers, reference to an "encapsulant" includes a single encapsulant as well as two or more different encapsulants, and the like.

In describing and claiming the present invention, the following terminology will be used in accordance with the definitions described below.

The term "hydrophobic" describes a substance that has a positive Log D value.

The term "hydrophilic" describes a substance that has a negative Log D value.

The term "Log D value" is used to describe the value of the logarithm of the distribution coefficient. The distribution coefficient is the ratio of the concentration of a compound in each of two phases of a mixture of n-heptane ("heptane") and water at equilibrium for the instance in which the pH of the water phase is adjusted to a prespecified pH. For this application, unless otherwise specified, the prespecified pH for measurements of the Log D value for an active ingredient, an encapsulant, delivery agent, or another component of a dosage form or composition as provided herein is the pH of the hydrophilic delivery agent for the dosage form. In an instance in which the hydrophilic delivery agent does not have a pH, or the pH is undefined, a pH of 7.4 is used, which is the physiological pH of blood serum. The Log D value can be described by the following equation, log D= $\log_{10}([\text{solute}]_{heptane}/[\text{solute}]_{water})$, where $[\text{solute}]_{heptane}$ and $[\text{solute}]_{water}$ refer to the concentration of the substance being measured in the heptane and water phases, respectively, for the measurement as described in this paragraph.

The term "slightly hydrophobic" describes a substance having a Log D value between 0.0 and 1.0.

The term "dosage form" refers to a solid or liquid material that comprises pharmaceutically acceptable ingredients, including an active ingredient, and is intended for administration to an animal or human subject. Dosage forms are typically administered for the purpose of dietary supplementation in areas of specific biological need (e.g., minerals, nutrients, or vitamins), alleviation of symptoms associated with a disease or condition, treatment of a disease or condition, or prevention of a disease or condition.

The term "active ingredient" refers to a biologically active substance. Examples of active ingredients include drugs, nutrients, minerals, proteins, botanicals, botanical extracts, vitamins, and vitamin derivatives. A cosmetic active ingredient is an ingredient or combination of ingredients that is/are effective to bring about a desirable change in one or more cosmetic skin or hair parameters. Examples include vitamin C, tocopherol, and sodium hyaluronate (hyaluronic acid), alpha and beta-hydroxy acids, ceramides, retinoic acid, etc.

The terms "solid, porous microcarrier with a hydrophobic surface" and "hydrophobic microcarrier" are used interchangeably herein and refer to a plurality of solid porous hydrophobic microcarriers having a maximum cross-sectional dimension of less than 1 mm for each microcarrier in the plurality. Solid, porous microcarriers with a hydrophobic surface can be, for example, natively hydrophobic, such as is the case with many polymeric microcarriers, or can be solid, porous microcarriers with a hydrophobically-modified surface. An example of solid, porous microcarriers with a hydrophobically-modified surface is described in detail in Example 1.

The term "encapsulant" refers to a material used to encase another material.

The term "delivery agent" refers to a substance in which one or more active ingredients are dispersed within a dosage form. For example, the active agent that is dispersed in the delivery agent may be associated with a plurality of porous microcarriers, each having a hydrophobic surface, optionally encapsulated in a hydrophobic encapsulant.

The term "tetracycline-class antibiotic" refers to tetracycline and tetracycline derivatives such as minocycline, doxycycline, oxytetracycline, and their corresponding pharmaceutically acceptable salt forms. A tetracycline antibiotic generally contains a four ring octahydrotetracene-2-carboxamide skeleton, while the actual substituents on the skeleton may vary.

The term "minocycline" refers to (4S,4aS,5aR,12aR)-4,7-bis(dimethylamino)-1,10,11,12a-tetrahydroxy-3,12-dioxo-4a,5,5a,6-tetrahydro-4H-tetracene-2-carboxamide (i.e. CAS number 10118-90-8) and its derivatives and salt forms. Exemplary forms of minocycline are commonly identified by their CAS numbers. For example, minocycline HCl has a CAS number of 13614-98J.

A "small molecule" may be defined broadly as an organic, inorganic, or organometallic compound typically having a molecular weight of less than about 1000. Preferred small molecules are organic in nature.

The term "ODS" refers to n-octadecylsilane.

The term "cosmetic" refers to an item as an "article intended to be rubbed, poured, sprinkled, or sprayed on, introduced into, or otherwise applied to the human body . . . for cleansing, beautifying, promoting attractiveness, or altering the appearance" (from U.S. FD&C Act, section 201(i)). The U.S. Food and Drug Administration classifies various items as cosmetics or drugs. This definition is intended to follow the U.S. FDA classifications. U.S. FDA further clarifies on its web site "Among the products included in this definition are skin moisturizers, perfumes, lipsticks, fingernail polishes, eye and facial makeup preparations, cleansing shampoos, permanent waves, hair colors, and deodorants, as well as any substance intended for use as a component of a cosmetic product."

The term "topical" refers to application to an exterior epithelial surface of the body, including the skin or cornea. For purposes of this application, applications inside a bodily orifice, such as the mouth, nose, or ear shall not be considered to be topical applications.

The term "reactive hydrophilic agents" refers to substances that are hydrophilic and are capable of reacting with an active ingredient of the dosage form to negatively affect the potency or another performance characteristic of the active ingredient, such as, for example, structural (i.e., chemical) or physical integrity.

"Pharmaceutically acceptable salt" denotes a salt form of a drug or active ingredient having at least one group suitable for salt formation that causes no significant adverse toxicological effects to the patient. Reference to an active ingredient as provided herein is meant to encompass its pharmaceutically acceptable salts, as well as solvates and hydrates thereof. Pharmaceutically acceptable salts include salts prepared by reaction with an inorganic acid, an organic acid, a basic amino acid, or an acidic amino acid, depending upon the nature of the functional group(s) in the drug. Suitable pharmaceutically acceptable salts include acid addition salts which may, for example, be formed by mixing a solution of a basic drug with a solution of an acid capable of forming a pharmaceutically acceptable salt form of the basic drug, such as hydrochloric acid, iodic acid, fumaric acid, maleic acid, succinic acid, acetic acid, citric acid, tartaric acid, carbonic acid, phosphoric acid, sulfuric acid and the like. Typical anions for basic drugs, when in protonated form, include chloride, sulfate, bromide, mesylate, maleate, citrate and phosphate. Suitable pharmaceutically acceptable salt forms and methods for identifying such salts are found in, e.g., Handbook of Pharmaceutical Salts: Properties, Selection and Use, Weinheim/Zürich: Wiley-VCH/VHCA, 2002; P. H. Stahl and C. G. Wermuth, Eds.

An active ingredient is said to be "associated with" a plurality of hydrophobic microcarriers if the active ingredient is contained within the pores of the microcarriers or is bound to the microcarriers ionically, covalently, or through other means, such as by Van der Waals forces, hydrogen bonding, or by other electrostatic interactions. Formulations in which an active ingredient is associated with a microcarrier can favorably impact active agent stability or release profile when compared to a formulation that lacks such an association.

The term "pharmaceutically acceptable" in reference to an entity or ingredient is one that may be included in the dosage forms provided herein and that causes no significant adverse toxicological effects in the patient at specified levels, or if levels are not specified, in levels known to be acceptable by those skilled in the art. All ingredients in the dosage forms described herein are provided at levels that are pharmaceutically acceptable. For clarity, active ingredients may cause one or more side effects and inclusion of the ingredients with a side effect profile that is acceptable from a regulatory perspective for such ingredients will be deemed to be "pharmaceutically acceptable" levels of those ingredients.

"Pharmacologically effective amount," "physiologically effective amount," and "therapeutically effective amount" are used interchangeably herein to mean the amount of a pharmaceutical preparation, or amount of an active ingredient in the pharmaceutical preparation, that is needed to provide a desired level of active ingredient in the bloodstream or in a target tissue. The precise amount will depend upon numerous factors, e.g., the particular active ingredient, the components and physical characteristics of the pharmaceutical preparation, intended patient population, patient considerations, and the like, and can readily be determined by one skilled in the art, based upon the information provided herein and available in the relevant literature.

The term "patient," refers to a living organism suffering from or prone to a condition that can be prevented or treated by administration of a dosage form as provided herein, and includes both humans and animals.

"Optional" or "optionally" means that the subsequently described circumstance may or may not occur, so that the description includes instances where the circumstance occurs and instances where it does not.

Overview

In certain circumstances, a hydrophilic active ingredient may be unstable in the presence of one or more reactive hydrophilic agents, such as the delivery agents described herein. To address this problem, the present application provides, in one aspect, a dosage form that is effective to physically separate an active ingredient such as a hydrophilic active agent from a reactive hydrophilic delivery agent, completely or to a large degree. The dosage form generally comprises (1) a hydrophilic active ingredient (or in certain instances, an active ingredient that is somewhat hydrophobic overall but has polar or ionic functional groups capable of reacting with the hydrophilic delivery agent), (2) a plurality of solid, porous microcarriers, each with a hydrophobic surface, (3) an optional hydrophobic encapsulant, and (4) a hydrophilic delivery agent. In one or more embodiments, the dosage form comprises a hydrophobic encapsulant. In some embodiments, an overcoat layer is added to the outside surface of the hydrophobic encapsulant. The hydrophilic active ingredient is associated with the plurality of hydrophobic microcarriers (wherein the association is described in greater detail below), and the microcarriers and active ingredient are optionally encapsulated by the hydrophobic encapsulant, and the resulting active ingredient associated with the plurality of hydrophobic microcarriers, which may be or not be in encapsulated form, is then mixed with a hydrophilic delivery agent. In one or more embodiments, the resulting dosage form is an emulsion. Such emulsions may, in certain instances, further comprise a surfactant, depending on the desired characteristics of the dosage form.

In yet one or more additional aspects, also provided is a dosage form comprising (1) a hydrophilic active ingredient (or in certain instances, an active ingredient that is somewhat hydrophobic overall but has polar or ionic functional groups capable of reacting with the hydrophilic delivery agent), (2) a plurality of solid, porous microcarriers, each with a hydrophobic surface, and (3) a hydrophobic encapsulant. The resulting dosage form may or may not comprise a further delivery agent or vehicle, wherein the delivery agent may be hydrophilic, hydrophobic or amphiphilic.

The Dosage Form

As described previously, the dosage form preferably comprises an active ingredient that is typically hydrophilic in nature, and is associated with a plurality of solid, porous microcarriers, each having a hydrophobic surface, a hydrophobic encapsulant that encapsulates each of the porous microcarriers associated with the active ingredient, and a hydrophilic delivery agent. The active ingredient may be contained within the pores of the microcarriers or may be bound to the microcarriers ionically, covalently, or by another means, such as by van der Waals forces, hydrogen bonding, or by other electrostatic bonding. In one particular embodiment, the active ingredient is contained within the porous microcarrier.

In one or more alternative embodiments, the dosage form comprises in a hydrophilic delivery agent, an active ingredient that is typically hydrophilic in nature, and is associated with the plurality of solid porous microcarriers each having a hydrophobic surface. In these embodiments, the active ingredient associated with the plurality of solid, porous microcarriers is not necessarily in encapsulated form.

In one or more further embodiments, the dosage form comprises an active ingredient that is typically hydrophilic in nature, and is associated with a plurality of solid, porous microcarriers, each having a hydrophobic surface, and a hydrophobic encapsulant that encapsulates each of the porous microcarriers associated with the active ingredient. In these embodiments, the encapsulated hydrophilic active ingredient associated with the solid, porous hydrophobic microcarrier may or may not be comprised within a hydrophilic delivery agent. In each of these embodiments, the active ingredient may be contained within the pores of the microcarriers or may be bound to the microcarriers ionically, covalently, or by another means, such as by van der Waals forces, hydrogen bonding, or by other electrostatic bonding. In one particular embodiment, the active ingredient is contained within the porous microcarrier.

In one or more embodiments, the Log D value of the outer surface of each of the solid, porous microcarriers with a hydrophobic surface is higher than the Log D value of the hydrophobic encapsulant. This reduces the interaction of the hydrophobic microcarriers with the hydrophilic delivery agent, thereby also limiting the interaction of the active ingredient with the hydrophilic delivery agent including any reactive hydrophilic agents therein. The reduced interaction of the hydrophobic microcarriers with the hydrophilic delivery agent also helps to maintain the stability of the active ingredient by maintaining the active ingredient within a more chemically inactive environment within the encapsulant. Log D values can be determined by measuring the octanol-water distribution coefficient via the conventional shake-flask method, or alternatively, one may employ an automated microfluidic liquid-liquid extraction methodology as described by Alimuddin, M., et al., in *J. Med. Chem.*, July 2008 (web version).

The dosage form can be produced by the following steps. Generally, a plurality of hydrophobic microcarriers is provided. An active ingredient is dissolved in a suitable solvent in which the active agent is soluble, such as, for example, ethanol to form a first solution. The plurality of hydrophobic microcarriers is then combined with the first solution to form a first mixture. Generally, at least a majority of the solvent from the first mixture is removed, e.g., by using heat and/or vacuum, to form a second mixture which is more concentrated than the first mixture, and in some cases, is substantially absent solvent. The second mixture is then combined with a hydrophobic encapsulant, and with a hydrophilic delivery agent (either simultaneously or in separate steps) to form the final dosage form. In some instances, the second mixture is combined with the hydrophobic encapsulant to form a third mixture, which is then combined with the hydrophilic delivery agent.

As an example, a plurality of hydrophobic microcarriers can be produced by mixing a plurality of hydrophilic, solid, porous microcarriers, a silane-coupling agent, and an (optional) solvent (for the silane-coupling agent) to form a mixture, and then heating the mixture. In instances in which a solvent is present, heating is carried out until the solvent is removed. In one or more embodiments, the heating step is performed under low pressure (i.e., at a pressure less than 0.2 atm) or under vacuum to enhance the rate of removal of the solvent. In one or more embodiments, the heating step is performed gradually (i.e., over a period of 10 minutes to 26 hours) to allow time for the silane-coupling agent to interact with the surface of the microcarriers.

Depending primarily on the active ingredient, the dosage form can be used to deliver an active agent, or as a dietary supplement, or as a cosmetic. In one or more embodiments, the dosage form is for administration of a small molecule drug. In one or more embodiments, the small molecule is an antibiotic or an antifungal agent, or a combination thereof. Illustrative classes of antibiotics include macrolides and the tetracyclines. One preferred class of antibiotics is the tetracyclines. For example, in one or more embodiments, the active ingredient is a small molecule macrolide antibiotic that is erythromycin. In yet another embodiment, the antibiotic is a tetracycline-type antibiotic selected from tetracycline, oxytetracycline, minocycline, and doxycycline. In yet another embodiment, the active ingredient is a triazole antifungal compound. Examples of such triazoles include itraconazole, fluconazole, isavuconazole, voriconazole, prmiconazole, ravuconazole, posaconazone, and ketoconazole. In one or more of preferred embodiments, the active ingredient comprises minocycline. In one or more preferred embodiments, the active ingredient comprises minocycline and the dosage form is for topical application to the skin for the treatment of acne.

Turning now to non-drug related applications, the dosage form may comprise as the active ingredient, a dietary supplement. Examples of such active ingredients include L-methylfolate, vitamin C, and choline hydroxide. In one or more embodiments, the active ingredient is classified as a cosmetic ingredient by the U.S. Food and Drug Administration, where an example of such an active ingredient is vitamin C, which as can be seen, may also be administered as a dietary supplement.

The solid, porous microcarriers, each with a hydrophobic surface can be, for example, natively hydrophobic, such as with many polymer microcarriers, or can be solid, porous microcarriers, each with a hydrophobically modified surface. An example of a solid, porous microcarrier having a hydrophobically-modified surface is described in more detail in Example 1.

Some materials that are naturally porous are particularly suited to be formed into porous microcarriers, such as amorphous silicates, crystalline nonlayer silicates, layer silicates, calcium carbonates, calcium/sodium carbonate double salts, sodium carbonates, clays, sodalites, alkali metal phosphates, chitin microbeads, carboxyalkylcelluloses, carboxyalkylstarches, cyclodextrins, porous starches, and mixtures thereof.

Some materials are particularly suited to forming hydrophobic microcarriers because the source material is hydrophobic. Examples of such hydrophobic materials include many of the synthetic polymer materials, such as, for example, low density polyethylene, high density polyethylene, polypropylene, polystyrene, polyacrylic acid and copolymers of polyacrylic acid and polystyrene, polyurethane, polyvinylchloride, polyvinylflouride, acrylonitrile-butadiene-styrene terpolymers, styrene-acrylonitrile copolymers, styrene butadiene copolymers, poly(4-methyl-pentene-1), polybutylene, polyvinylidene chloride, polyvinyl butyral, polyvinyl imidazole, chlorinated polyethylene, polyethylene oxide, ethylene-vinyl acetate copolymers, polyvinyl acetate, polyvinyl alcohol, polymethyl-methacrylate, polymethyl-acrylate, ethylene-acrylic acid copolymers, ethylene-acrylic acid metal salt copolymers, chlorosulphonate polyolefins, polyesters such as polyethylene teraphthalate and polybutylene teraphthalate, polyamides such as Nylon 6, Nylon 11, Nylon 13, Nylon 66, polycarbonates and polysulfones, and polyarylene and polyalkylene oxides; agrose, cellulose, gelatin, alginate, elastin, chitosan, poly(lactides), poly(glycolides), poly(lactide-co-glycolides), poly(lactic acids), poly (glycolic acids), poly(lactic acid-co-glycolic acids), polycaprolactone, polycarbonates, polyesteramides, polyanhydrides, poly(amino acids), polyorthoesters, poly (hydroxyalkanoates), polyacetyls, polycyanoacrylates, polyetheresters, poly(esters), poly(dioxanone), poly(alkylene alkylates), copolymers of polyethylene glycol and a polyorthoester, poly(hydroxy acids), poly(lactones), poly (amides), poly(ester-amides), poly(amino acids), poly(anhydrides), poly(ortho-esters), poly(carbonates), poly(phosphazines), poly(thioesters), polysaccharides and mixtures, blends and copolymers thereof. The use of a hydrophobic material to form the microcarrier is advantageous because, in many cases, no additional surface modification is required.

Preferably, one or more of the hydrophobic microcarriers preferably has a largest crosssectional dimension in the range of 1 nm to 200 µm, and more preferably a range selected from 1 µm to 200 µm, 1 µm to 100 µm, or 5 µm to 50 µm. A plurality of porous microcarriers can be fabricated by many methods. For example, porous microcarriers can be produced by chemical reactions that form any of a number of preferred structural features. Examples of such reactions include the sol-gel glass transition method, crystallization reactions, selective chemical etching, reactive ion etching, and thermal decomposition. Additionally, mechanical processing methods, such as spray drying, electric discharge machining (EDM), and mechanical fracturing, can be used. Porous microstructures can also be made from inorganic materials, such as metal oxides, such as $SiO_2$, $Al_2O_3$, $AlPO_4$, $MgO$, $TiO_2$, and $ZrO_2$, metal silicates, metal carbonates, metal phosphates, and metal sulfates. Porous microstructures can also be made from natural clay, sugar alcohols, sugars and cellulose and cellulose derivatives. Porous microstructures can also be zeolitic in nature (e.g., linde type X zeolite, linde type Y zeolite, or macroporous zeolites) or prepared from active carbon particles. Porous microcarriers can also be prepared by appending ionic crystals of metal ions to porous structures using spray drying or heat decomposition. Examples of such metal ions include $Na^+$, $K^+$, $Ti^{4+}$, $Mg^{2+}$, $Zr^{2+}$, $Zn^{2+}$, $Fe^{2+}$, $Fe^{3+}$, $Al^{3+}$, $Co^+$, $Ta^{5+}$, $Ni^{2+}$, $Cu^{1+}$, $Cu^{2+}$, and $Si^{4+}$. Porous microcarriers can be porous synthetic or natural polymer microcarriers. Examples of suitable polymers for making porous microcarriers include thermoplastic organic polymers, polyacetals, polyamides, polyesters, polyurethanes, polysiloxanes, polyoxiranes, polydienes, polystyrenes, polymethacrylates, polyvinyl chloride, polyamides and polyolefins. Polyolefins, such as polyethylene and polypropylene, are preferred examples of polymers. The polymers may be homopolymers or copolymers. Suitable materials and methods for fabricating porous microcarriers are well known to those skilled in the art.

In one or more embodiments, the surface of the hydrophilic microcarriers is modified to increase its hydrophobicity by a silane-coupling reaction, such as described by Fomitchev, et al. in U.S. Pat. No. 8,435,474, to thereby covalently attach hydrophobic hydrocarbon groups to the microcarrier surface. Illustrative surface groups include C1-022, although any suitable hydrocarbon attachment may be employed. Thus, the microcarrier surface can be modified by covalent attachment of C-1, C-2, C-3, C-4, C-5, C-6, C-7, C-8, C-9, C-10, C-11, C-12, C-13, C-14, C-15, C-16, C-17, C-18, C-18, C-20, C-21, C-22, and so forth. An illustrative hydrocarbon modification used herein is C-18. For example, a silane-coupling agent (e.g., a trialkoxysilane compound) is used to add hydrocarbon chains to one or more surfaces of the hydrophilic microcarriers. Examples of silane-coupling agents include trimethoxy(octadecyl)silane, methyltrimethoxysilane, ethyltrimethoxysilane, propyltrimethoxysilane, butyltrimethoxysilane, pentyltrimethoxysilane, hexyltrimethoxysilane, heptyltrimethoxysilane, octyltrimethoxysilane, nonyltrimethoxysilane, decyltrimethoxysilane, undecyltrimethoxysilane, dodecyltrimethoxysilane, tetradecyltrimethoxysilane, stearyltrimethoxysilane, methyltriethoxysilane, ethyltriethoxysilane, propyltriethoxysilane, butyltriethoxysilane, pentyltriethoxysilane, hexyltriethoxysilane, heptyltriethoxysilane, octyltriethoxysilane, nonyltriethoxysilane, decyltriethoxysilane, undecyltriethoxysilane, dodecyltriethoxysilane, tetradecyltriethoxysilane, stearyltriethoxysilane, and combinations thereof. Preferably, the silane-coupling agent is selected from the group consisting of trimethoxy(octadecyl)silane, hexyltrimethoxysilane, heptyltrimethoxysilane, octyltrimethoxysilane, nonyltrimethoxysilane, decyltrimethoxysilane, undecyltrimethoxysilane, dodecyltrimethoxysilane, tetradecyltrimethoxysilane, stearyltrimethoxysilane, methyltriethoxysilane, ethyltriethoxysilane, propyltriethoxysilane, butyltriethoxysilane, pentyltriethoxysilane, hexyltriethoxysilane, heptyltriethoxysilane, octyltriethoxysilane, nonyltriethoxysilane, decyltriethoxysilane, undecyltriethoxysilane, dodecyltriethoxysilane, tetradecyltriethoxysilane, stearyltriethoxysilane, 3-aminopropyltriethoxysilane, 3-aminobutyltriethoxysilane, 3-aminobutyltriethoxysilane, and combinations thereof.

In one or more preferred embodiments, the outermost surface of each hydrophobic microcarrier is hydrophobic and one or more pore surfaces are hydrophilic. One method for fabricating such structures is to use a silane-coupling agent to add hydrocarbon chains to the surface of the hydrophilic microcarriers. This approach is particularly effective if a reactive hydroxyl group that reacts with the silane-coupling agent is located primarily on the surface of each of the microcarriers. Examples of such hydrophilic microcarriers include, for example, metal oxides (e.g., $SiO_2$, $Al_2O_3$, and zeolites), metal salts (e.g., $CaCO_3$, $CaPO_4$, and $MgCO_3.Mg(OH)_2.nH_2O$), or organic polymer compounds (e.g., polyethylene and polystyrene).

Microstructures can also be fabricated as described by Badri et al. in U.S. Patent Application No. US 2012-0219728 A1, which is herein incorporated by reference. In this process, hydrophilic microcarriers are modified to produce microcarriers each with a hydrophobic outer surface and one or more hydrophilic pore surfaces. Yet in another approach for fabricating such microcarriers, as described by Mao et al. (see, e.g., U.S. Patent Application No. US 2003-0134100 A1, which is herein incorporated by reference, hydrophobic porous polymer microcarriers are modified to make their pore surfaces hydrophilic. The use of hydrophobic microcarriers having an outermost hydrophobic surface and one or more internal pore surfaces that are hydrophilic may allow more facile incorporation of a hydrophilic active ingredient into such a structure.

The hydrophobic encapsulant is hydrophobic and is typically immiscible with water. Examples of hydrophobic encapsulants include synthetic waxes (e.g., polyethylenes; polyamides; polystyrenes; polyisoprenes; polycarbonates; polyesters; polyacrylates; polyureas; polyurethanes; polyolefins; polysaccharides; epoxy resins; vinyl polymers; Fischer-Tropsch waxes, with or without chemical modification), semi-synthetic waxes (e.g., amide waxes and montane waxes); natural waxes (e.g., beeswax and carnauba wax), petrolatum waxes, and combinations thereof).

In one or more embodiments, the hydrophobic encapsulant is a liquid or semi-liquid compound. Examples include hydrocarbon-based oils, silicone oils, fluoro oils, non-fluoro oils, and combinations thereof. Such oils may be in volatile or in non-volatile forms. Examples of volatile oils include linear or cyclic silicone oils, especially those containing from 2 to 10 silicon atoms or from 2 to 7 silicon atoms. These silicones optionally comprise alkyl or alkoxy groups containing from 1 to 10 carbon atoms. Examples include dimethicones, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and combinations thereof. Examples of non-volatile oils include synthetic oils, petrolatum oils, and natural oils such as, shea oil, alfalfa oil, poppy-seed oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flaxseed oil, rapeseed oil, cottonseed oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant seed oil, kiwi seed oil, grapeseed oil, pistachio oil, winter squash oil, pumpkin oil, quinoa oil, musk rose oil, sesame oil, soybean oil, sunflower oil, castor oil and watermelon oil, and combinations thereof.

Finally, the dosage form includes a hydrophilic delivery agent or carrier for the plurality of solid, porous microcarriers having a hydrophobic surface and an active ingredient associated therewith, wherein the microcarriers are in encapsulated form. Examples of hydrophilic delivery agents include gels, creams, aqueous agents, non-aqueous agents, or aqueous agents with at least 10% water content. Examples of non-aqueous solvents include dimethyl sulfoxide (DMSO), N-methyl pyrollidone (NMP), tetraglycol, polyethylene glycol, polypropylene glycol, glycerol, and propylene glycol. In one or more embodiments, the dosage form comprises a gelling agent to stabilize a hydrophobic emulsion. In one or more embodiments, the dosage form comprises an emulsifier, particularly in cases where smaller micelle size is desired than would be accomplished without the emulsifier or where an emulsifier provides added stability to the formulation by maintaining separation of the active ingredient and the hydrophilic delivery agent. Example of emulsifiers include lectin, mustard, soy lectin, sodium stearoyl lactylate, diacetyl tartaric ester of monoglyceride, emulsifying wax, cetearyl alcohol, polysorbate 20, and ceteareth 20. Many types of surfactant materials can be used as emulsifiers. The selection of a suitable emulsifier will be based on the desired properties of the final formulation/dosage form.

The final dosage form may be in a number of different forms, including, for example, liquids, gel caps, sprays, foams, pills, tablets, and capsules. Developing such dosage forms can be performed by one skilled in the art. For additional information regarding these different forms, see, for example, "Remington: The Science and Practice of Pharmacology," 22nd edition, (Pharmaceutical Press, 2013).

In one or more preferred embodiments, the dosage form is for topical use. For example, the dosage form can be applied to the skin surface during use. Without loss of generality, the embodiments described herein are in the form of a liquid. Other forms will be evident to those skilled in the art.

Turning now to consideration of the Examples, Example 1 illustrates a dosage form wherein the microcarrier is a silica-based porous material having a particle size on the average of 30-40 microns, where the silica surface was modified by silylation with an illustrative silylating reagent, trimethoxy(octadecyl)silane, although any of the illustrative silylating reagents described herein is suitable for providing hydrophobic surface modification of the microcarrier. The silica-based material comprises microspheres, and also possesses a high surface area of about 300 $m^2/g$. Thus, in one preferred embodiment, the instant dosage form comprises a silicon dioxide microcarrier modified to possess a hydrophobic surface by covalent attachment of C-18 groups such as described In Example 1. Specifically, minocycline was mixed with the C-18 surface-modified silicon dioxide microcarrier to form a powder comprising drug associated with the microcarrier; this powder was then mixed with an exemplary encapsulating agent, in this instance, mineral oil, to provide encapsulated drug, where the drug was associated with the microcarrier. The encapsulated drug-hydrophobic microcarrier combination was then suspended in a hydrophilic delivery vehicle. Fluorescent microscopy revealed that the active agent was effectively sequestered from the hydrophilic delivery vehicle by virtue of its association with the microcarrier, and the encapsulation of the drug-microcarrier combination. Thus, this example illustrates the successful partitioning/sequestration of the drug-hydrophobic microcarrier combination from the hydrophilic delivery agent. Thus, in one preferred embodiment, the dosage form comprises a tetracycline drug, a hydrophobically surface-modified silicon dioxide-based microcarrier associated with the tetracycline drug, and a hydrophilic delivery vehicle, where the drug-microcarrier combination is in encapsulated form and dispersed in the hydrophilic delivery agent.

Briefly, Example 2 illustrates, when considered in view of Example 1, the advantages of using a hydrophobically-modified microcarrier in the dosage form to effect successful partitioning of the active agent from the hydrophilic delivery agent. In sum, a non-surface modified microcarrier, in this case, the silica-based porous microcarrier from Example 1 but in its non-surface modified form (i.e., absent covalently attached hydrocarbon groups), was ineffective in sequestering the active agent from the delivery agent. As can be seen in the related figures, the active ingredient did not remain associated with the microcarrier, even upon encapsulation but rather leaked into the hydrophilic delivery agent and dissolved therein. Similarly, Example 4 provides an additional example of a dosage form comprising a hydrophilic active agent, in this case, stabilized by the addition of magnesium, combined with a non-hydrophobically modified microcarrier and an encapsulating agent, where the resulting dosage form not only failed to protect the active agent-microparticles via encapsulation, but additionally indicated degradation of the active agent, presumably due to its direct exposure to the hydrophilic delivery medium.

Example 3 illustrates the advantage of further stabilizing the active ingredient, in this instance, minocycline, in the form of its pharmaceutically acceptable salt, by incorporation of a magnesium salt into the dosage form. As can be seen in FIGS. 3A and 3B, the incorporation of magnesium did not disrupt the partitioning of the drug from the hydrophilic delivery agent; indeed fluorescence microscopy clearly shows the effective sequestration of the active agent-microparticle combination within the encapsulant, where the encapsulated active agent is dispersed within the hydrophilic delivery medium. Thus, in one or more preferred embodiments, a dosage form as provided herein comprises a tetracycline drug combined with a divalent or trivalent cation such as magnesium, calcium, zinc, or gallium, in the form of a salt. Illustrative salts for incorporation into the dosage form include magnesium chloride, magnesium bromide, magnesium sulfate, calcium chloride, calcium bromide, calcium sulfate, zinc chloride, gallium chloride, magnesium citrate, magnesium acetate, and the like.

Example 5 provides the hydrophobicity of several exemplary microcarrier materials. Preferred microcarriers are those that are hydrophobic, i.e., having a positive Log D. Thus, in one or more preferred embodiments, a microcarrier for use in the instant dosage forms is selected from hydrocarbon-surface modified silica (e.g., surface modified with C1-C-22 hydrocarbon groups), surface-modified microtubular basic magnesium carbonate (e.g., surface modified with C1-C-22 hydrocarbon groups), and microcarriers prepared from polyacrylates such as the spherical polymers referred to generally as TECHPOLYMER. Illustrative microcarriers include those belonging to the MBX series (a crosslinked polymethylmethacrylate polymer), the SBX series (a cross-linked polystyrene spherical particle), the MSX SMX series (a copolymerized cross-linked particle of methyl methacrylate and styrene), the SSX series (monodisperse crosslinked polymethylmethacrylate spherical polymer particles), the BMX series (a cross-linked polybutylmethacrylate spherical particle), the ABX, ARX, and AFX series (cross-linked polyacrylic ester spherical particles), and the MB and MBP series (polymethylmethacrylate spherical particles). In one or more preferred embodiments, the microcarrier is a cross-linked polymethylmethacrylate polymer.

Example 6 provides log D measurements for the exemplary hydrophilic drug, minocycline, combined with a number of different exemplary microcarriers. The values provide an indication of the hydrophobicity of various active agent-microcarrier combinations, where the combination optionally contains an additional overcoat material as indicated in Table 4.

Example 7 further describes the advantages of hydrocarbon surface modification of a non-hydrophobic silica microcarrier in terms of improving its partitioning index (i.e., ability to partition the active ingredient from a hydrophilic delivery medium by virtue of, e.g., encapsulation).

Example 8 describes an additional embodiment of the instant dosage forms wherein the encapsulated active agent-microcarrier combination is further sequestered from the hydrophilic delivery medium by virtue of an additional boundary layer (i.e., overcoat layer) surrounding the encapsulation layer. Although an overcoating can be provided by any suitable overcoating material as described herein, in one or more embodiments, the overcoat layer is provided by polymerization of ethyl 2-cyanoacrylate for form an acrylate-based overcoat layer.

EXAMPLES

The following examples are put forth to provide those of ordinary skill in the art with a complete disclosure and description of how the dosage form, its components, active ingredients, microparticles, encapsulant, delivery system, and the like, are prepared and evaluated, along with related methods, and are intended to be purely exemplary. Thus, the examples are in no way intended to limit the scope of what the inventors regard as their invention. There are numerous variations and combinations of reaction conditions, e.g., component concentrations, desired solvents, solvent mixtures, temperatures, pressures, and other reaction parameters and conditions that may be employed to optimize dosage form characteristics such as purity, yield, stability, and the like. Such are considered as well within the scope of the present disclosure.

Example 1

Dosage Form Comprising Surface-Modified Microcarriers and an Antibiotic

A dosage form was produced in accordance with the teachings herein, and demonstrates certain aspects thereof. The dosage form was prepared from the materials listed in Table 1. A plurality of solid, porous microcarriers, each with a hydrophobic surface was prepared. Specifically, a plurality of hydrophilic solid, porous microcarriers (granulated colloidal silicon dioxide (AEROPERL 300 PHARMA), a silane coupling agent (trimethyoxy(octadecyl)silane), and a suitable solvent (toluene) were combined to form a mixture. The microcarriers employed have an average particle size of 30 to 40 microns, and are mesoporous, having a pore volume of about 1.6 ml/g. The reaction mixture was heated under vacuum in a rotary evaporator (Buchi Labortechnik AG, Flawil, Switzerland) starting at a temperature of 100° C. over a period of 30 minutes to remove the solvent. The mixture heating continued until the solvent was removed, over a period of approximately 2 hours. This process formed a plurality of hydrophobic microcarriers by virtue of surface modification using a suitable silane reagent, i.e., trimethoxy(octadecyl)silane.

TABLE 1

Materials for preparation of dosage form for Example 1

| Material | Example | Source of example material | Amount of material |
|---|---|---|---|
| Microcarrier | granulated colloidal silicon dioxide (AEROPERL 300 PHARMA) | Evonik Industries AG, Essen, Germany | 0.39 g |
| Silane coupling agent | trimethoxy(octadecyl)silane | Sigma-Aldrich, St. Louis, MO | 0.12 g |
| Solvent (i.e., for the silane coupling agent) | toluene | Sigma-Aldrich, St. Louis, MO | 26.0 g |
| Active ingredient | minocycline | Hovione Inter Ltd., Loures, Portugal | 0.2452 g |
| Solvent for the active ingredient | ethanol | Spectrum Chemical Mfg. Corp., New Brunswick, NJ | 10 g |
| Hydrophobic encapsulant | mineral oil (USP grade) | Sigma-Aldrich, St. Louis, MO | 0.3 g |
| Hydrophilic delivery agent | polycarbophil/propylene glycol gel | The Lubrizol Corporation (Walnut Creek, CA) | 0.3 g |

Then, an active ingredient (minocycline) was dissolved in a suitable solvent (ethanol) to form a minocycline-ethanol solution, the plurality of hydrophobic microcarriers (0.5103 g) was mixed into the minocycline-ethanol solution until the microcarriers were well dispersed within the solution. The ethanol was removed from the resulting mixture by evaporating at 60° C. at 10 mbar using a rotary evaporator (Buchi Labortechnik AG, Flawil, Switzerland) to form a powder. The resulting powder (0.1629 g) was then mixed with 0.3 g of mineral oil (USP grade, Sigma-Aldrich), which in this case, served as the encapsulating agent. The mixture of the powder and the mineral oil was then suspended in an exemplary delivery agent (3 g of non-aqueous gel, prepared from 2% (w/w) polycarbophil/propylene glycol gel (i.e., the hydrophilic delivery agent). The mixture was then emulsified manually using a spatula and a vortex mixer to provide the desired dosage form.

Although a non-aqueous gel was employed in this example, aqueous delivery agents, such as aqueous gels, can be used as alternatives in place of the non-aqueous gel.

The product was assessed by microscopy to determine the location of the active ingredient, minocycline, within the dosage form. Due to its fluorescence, the location of the minocycline in the dosage form was confirmed by fluorescent microscopy with an excitation wavelength in the range of 380-430 nm and an emission wavelength filter to filter out wavelengths below 600 nm (other components of the dosage form were not fluorescent). A representative sample of the resulting images is presented as FIGS. 1A-1F, FIGS. 1A, 1B, 1C, and 1E were captured using illumination with a standard white filament bulb. FIGS. 1D and 1F capture the same portion of the dosage form as shown in FIGS. 1C and 1E, respectively, illuminated with a UV light source to capture fluorescence from the active ingredient, minocycline.

In the color versions of the images shown in FIG. 1, the active ingredient, minocycline, appeared yellowish brown when illuminated with a standard white filament bulb and pinkish under illumination with an UV light source. Thus, the location of the active ingredient within the dosage form was distinguished and its approximate concentration distribution determined by examining microphotographs of the dosage form.

As shown in FIGS. 1A-1F, a high concentration of minocycline in the dosage form caused some of the active ingredient to be crowded close to the boundary between the hydrophobic encapsulant and the hydrophilic delivery agent. By reducing the density of the microparticles within the hydrophobic phase, the active ingredient can be better confined at a location in the dosage form that is distant from this boundary. As a result, the active agent will possess greater stability by virtue of having less direct interaction with the hydrophilic delivery agent. If a lesser density of microparticles is used for a predefined concentration of the active ingredient in the composition, then the amount of the active ingredient associated with each microparticle will be larger. This may negatively affect the hydrophobicity of the microparticle. So, for a specified concentration of the active ingredient, there may be an optimal density of microparticles for a particularly selected microparticle and active ingredient. However, most notably, the approach described herein, i.e., the use of hydrophobic-modified microcarriers, when combined with an encapsulating agent and a hydrophilic carrier, was effective to provide a formulation having the active agent primarily in encapsulated form. The illustrative active agent, minocycline, is effectively sequestered from the hydrophilic carrier, to thereby provide a protective barrier from the potential degrading and/or deleterious effects of the hydrophilic carrier material.

Example 2

Dosage Form Comprising Non-Surface-Modified, Hydrophilic Microcarriers and an Antibiotic A dosage form was produced using a plurality of hydrophilic microcarriers instead of a plurality of hydrophobic microcarriers to demonstrate the difference in the two approaches, and the benefits associated with use of a hydrophobic microcarrier. The dosage form was fabricated as described in Example 1, with the following modifications: (1) in the first step of the process, a surface-modification step was omitted (formation of a plurality of hydrophobic microcarriers) and (2) in the third step, granulated colloidal silicon dioxide (AEROPERL 300 PHARMA) (0.5103 g), which has a hydrophilic surface, was mixed into the minocycline-ethanol solution in the place of the plurality of hydrophobic microcarriers.

Assessment of the dosage form was performed by microscopy and fluorescence microscopy as in Example 1. A representative image is shown in FIG. 2. In color versions of the image shown in FIG. 2, the yellowish brown color of the minocycline was distributed broadly throughout the hydrophilic delivery agent and was not confined within the hydrophobic encapsulant regions (i.e., bubbles) of the dosage form. In fact, the minocycline and hydrophilic delivery system were preferentially excluded from the hydrophobic regions of the dosage form. The minocycline was originally associated with the microcarrier, but after exposure to the delivery agent, the minocycline became dissolved therein. In the resulting dosage form, the active ingredient (i.e., minocycline) is susceptible to exposure to hydrophilic reactive agents that are incorporated into or present in the hydrophilic delivery agent and capable of degrading the active ingredient.

Example 3

Dosage Form Comprising Surface-Modified Microcarriers and a Magnesium-Stabilized Antibiotic The encapsulation demonstrated in Example 1 provided a physical separation of a hydrophilic active ingredient and a hydrophilic delivery agent. Additional stability can be accomplished by further stabilizing the active ingredient. For example, minocycline can be stabilized with magnesium or by other methods known to those skilled in the art. A dosage form was fabricated as described in Example 1, substituting magnesium stabilized minocycline in place of minocycline.

(AEROPERL 300 PHARMA), a silane coupling agent (trimethoxy(octadecyl)silane), and a suitable solvent (toluene) were combined to form a mixture. The microcarriers employed have an average particle size of 30 to 40 microns, and are mesoporous, having a pore volume of about 1.6 ml/g. The reaction mixture was heated under vacuum in a rotary evaporator (Buchi Labortechnik AG, Flawil, Switzerland) starting at a temperature of 100° C. over a period of 30 minutes to evaporate the solvent. The mixture heating continued until the solvent was removed, over a period of approximately 2 hours. This process formed a plurality of hydrophobic microcarriers by virtue of surface modification with a suitable silane reagent.

TABLE 2

Reagents Used to Prepare Dosage Form

| Material | Example | Source of example material | Amount of material |
|---|---|---|---|
| Microcarrier | granulated colloidal silicon dioxide (AEROPERL 300 PHARMA) | Evonik Industries AG, Essen, Germany | 0.39 g |
| Silane coupling agent | trimethoxy(octadecyl)silane | Sigma-Aldrich, St. Louis, MO | 0.12 g |
| Solvent for the silane coupling agent | toluene | Sigma-Aldrich, St. Louis, MO | 26.0 g |
| Active ingredient | minocycline HCl | Hovione Inter Ltd., Loures, Portugal | 2.0 g |
| Stabilizing agent | magnesium chloride | Sigma-Aldrich, St. Louis, MO | 1.14 g |
| Solvent for the active ingredient | ethanol | Spectrum Chemical Mfg. Corp., New Brunswick, NJ | 40 mL (~30 g) |
| Hydrophobic encapsulant | mineral oil (USP grade) | Sigma-Aldrich, St. Louis, MO | 0.3 g |
| Hydrophilic delivery agent | polycarbophil/propylene glycol gel | The Lubrizol Corporation (Walnut Creek, CA) | 0.3 g |

2.0 g of minocycline HCl and 1.14 g of magnesium chloride were dissolved in 20 mL of ethanol to form a solution with a molar ratio of magnesium to minocycline of about 3:1. The solution was heated in a rotary evaporator to 60° C. at 10 mbar to remove the ethanol. A portion (0.1 g) of the resulting powder was dissolved in 20 mL of ethanol. 0.3 g of the hydrophobic microcarrier was added to the resulting solution. The resulting mixture was heated in a rotary evaporator to 50° C. at 50 mbar to remove the ethanol. The resulting powder of stabilized minocycline associated with a plurality of hydrophobic microcarriers was suspended in 1 mL of mineral oil as the encapsulating agent. The mixture of the powder and the mineral oil was then suspended in a delivery agent (3 g of non-aqueous gel, prepared from 2% (w/w) polycarbophil/propylene glycol gel (i.e., the hydrophilic delivery agent). The mixture was then emulsified manually using a spatula and a vortex mixer to provide the desired dosage form.

Assessment of the dosage form was performed by microscopy and fluorescence microscopy as in Example 1. A representative set of images is shown in FIGS. 3A and 3B. In color versions of FIG. 3A, the minocycline has a yellowish brown color and was indeed localized to the hydrophobic portions (bubbles) of the dosage form. This was confirmed by the fluorescence microscopy. In the color version of the image shown in FIG. 3B the minocycline which, appears as a bright pink color, was confined to the hydrophobic portions of the dosage form. In such a dosage form, the minocycline active ingredient was protected by both the encapsulation within the hydrophobic encapsulant and by stabilization via the incorporation of magnesium.

Example 4

Dosage Form Comprising Non-Surface-Modified, Hydrophilic Microcarriers and a Magnesium-Stabilized Antibiotic A dosage form was produced using a plurality of hydrophilic microcarriers instead of a plurality of hydrophobic microcarriers to further demonstrate the importance of using hydrophobic microcarriers. A dosage form was fabricated as described in Example 2 and substituting magnesium-stabilized minocycline as described in Example 3 above in place of minocycline.

The dosage form was prepared from the materials listed in Table 3. A plurality of solid, porous microcarriers, each with a hydrophobic surface was prepared. Specifically, a plurality of hydrophilic solid, porous microcarriers (granulated colloidal silicon dioxide (AEROPERL 300 PHARMA), a silane coupling agent (trimethoxy(octadecyl)silane), and a suitable solvent (toluene) were combined to form a mixture. The microcarriers employed have an average particle size of 30 to 40 microns, and are mesoporous, having a pore volume of about 1.6 ml/g. The reaction mixture was heated under vacuum in a rotary evaporator (Buchi Labortechnik AG, Flawil, Switzerland) starting at a temperature of 100° C. over a period of 30 minutes to evaporate the solvent. The heating continued until the solvent was removed, over a period of approximately 2 hours. This process formed a plurality of hydrophobic microcarriers by virtue of surface modification with a suitable silane reagent. Any of the silylating reagents described herein are suitable for surface modification.

TABLE 3

Materials for preparation of dosage form for Example 3

| Material | Example | Source of example material | Amount of material |
|---|---|---|---|
| microcarrier | granulated colloidal silicon dioxide (AEROPERL 300 PHARMA) | Evonik Industries AG, Essen, Germany | 0.39 g |
| silane coupling agent | trimethyoxy(octadecyl)silane | Sigma-Aldrich, St. Louis, MO | 0.12 g |
| solvent for the silane coupling agent | toluene | Sigma-Aldrich, St. Louis, MO | 26.0 g |
| active ingredient | minocycline HCl | Hovione Inter Ltd., Loures, Portugal | 2.0 g |
| stabilizing agent | magnesium chloride | Sigma-Aldrich, St. Louis, MO | 1.14 g |
| solvent for the active ingredient | ethanol | Spectrum Chemical Mfg. Corp., New Brunswick, NJ | 40 mL (~30 g) |
| hydrophobic encapsulant | mineral oil (USP grade) | Sigma-Aldrich, St. Louis, MO | 0.3 g |
| hydrophilic delivery agent | polycarbophil/propylene glycol gel | The Lubrizol Corporation (Walnut Creek, CA) | 0.3 g |

2.0 g of minocycline HCl and 1.14 g of magnesium chloride were dissolved in 20 mL of ethanol to form a solution with a molar ratio of magnesium to minocycline of about 3:1. The solution was heated in a rotary evaporator to 60° C. at 10 mbar to remove the ethanol. A portion (0.1 g) of the resulting powder was dissolved in 20 mL of ethanol. 0.3 g of the hydrophobic microcarrier was added to the resulting solution. The resulting mixture was heated in a rotary evaporator to 50° C. at 50 mbar to remove the ethanol. The resulting powder of stabilized minocycline associated with a plurality of hydrophobic microcarriers was suspended in 1 mL of mineral oil as the encapsulating agent. The mixture of the powder and the mineral oil was then suspended in a delivery agent (3 g of non-aqueous gel, prepared from 2% (w/w) polycarbophil/propylene glycol gel (i.e., the hydrophilic delivery agent). The mixture was then emulsified manually using a spatula and a vortex mixer to provide the desired dosage form.

Figure 4A:
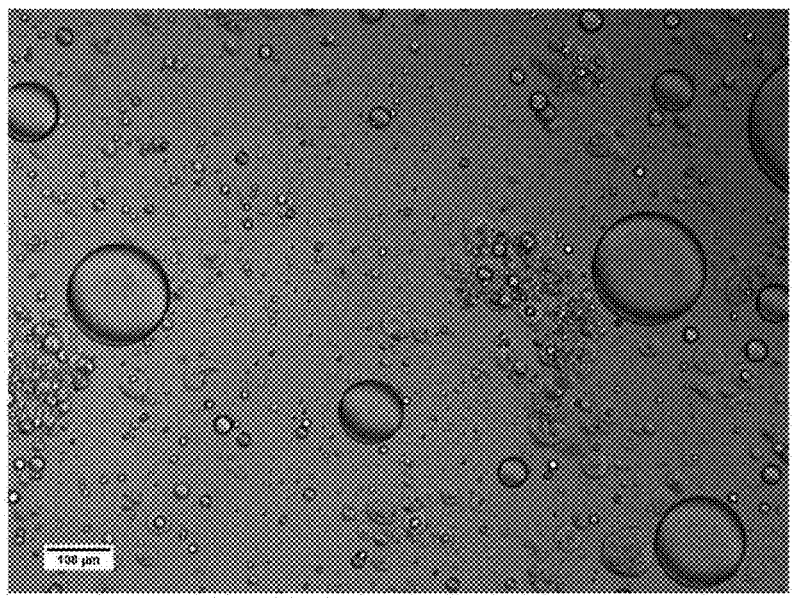
FIGS. 4A and 4B are microscope images of an exemplary dosage form produced in accordance with Example 4. The image in FIG. 4A was captured under white light illumination. The image in FIG. 4B shows fluorescence from the illustrative active ingredient, minocycline, stabilized with magnesium, when illuminated under UV light.
Figure 4B:
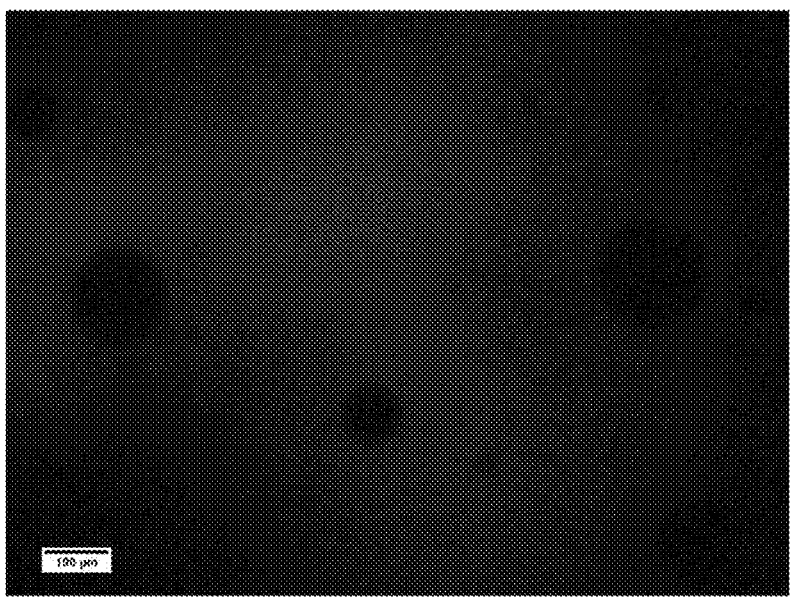

Assessment of the resulting dosage form was performed by microscopy and fluorescence microscopy as in Example 3. A representative set of images is shown in FIGS. 4A and 4B. In the color version of FIG. 4A, there was no yellowish brown color for the minocycline. The absence of active minocycline was confirmed on the color version of the fluorescence microscopy image shown in FIG. 4b. Minocycline was not visible, even under fluorescence because it was significantly degraded by reactions with hydrophilic reactive agents in the hydrophilic delivery agent.

Example 5

Comparison of Solid, Porous Microcarriers: Log D Measurements

A set of experiments was performed to compare the hydrophobicity of several different types of solid, porous microcarriers. The results of these experiments are summarized in Table 4.

Each of the test materials was evaluated according to a standard process. Each test material consisted essentially of a plurality of microcarriers. The measurement included the following steps: 1) 80 mg of the test material was mixed with 0.8 mL of heptane in a 2 ml test tube in a vortex mixer at 3200 rpm. 2) 0.8 mL of water was added to the test tube and mixed by the vortex mixer for 2 seconds at 3200 rpm. 3) The mixture was held stationary for approximately 3 minutes to allow the separation of the heptane and water phases. 4) 0.5 mL samples from each phase were transferred to clean test tubes. 5) The test tubes were then placed in a drying oven at 60° C. in vacuum for 12 hours to evaporate the water and heptane. 6) The mass of the remaining dry powder in each test tube was measured and the ratio was calculated to measure log D as follows: Log D=Log 10 ((mass of dried powder from heptane phase)/(mass of dried powder from water phase)). Note that in parallel with step 4, the pH of the water phase of the solution was recorded.

TABLE 4

Measurement of Log D for a plurality of microcarriers of different types

| Sample # | Carrier material | Log D | pH |
|---|---|---|---|
| Aeroperl | hydrophilic silica (Evonik Industries AG, Essen, Germany, part number AEROPERL 300 PHARMA) | −2.7 | 5.7 |
| 021014A | ODS-modified silica (silicon dioxide) | 1.8 | 7.2 |
| Magnesium | $Mg(OH)_2MgCO_3$ microtubules (Nittetsu Mining Co., Tokyo, Japan) | −2.6 | 10.2 |
| 021414B | Lauric acid-modified $Mg(OH)_2MgCO_3$ | 2.0 | 8.9 |
| Techpolymer | Cross-linked polymethylmethacrylate polymer, spherical polymer particles (Techpolymer MBP-8, which has an average particle diameter of about 8 micrometers, a high degree of crosslinking, and a typical micropore diameter of about 20 nm) | 1.1 | 8.4 |

The results of these measurements are shown in Table 4. These results demonstrate that hydrophobic microparticles can be produced from a variety of materials, including silica, microtubular basic magnesium carbonate ($Mg(OH)_2MgCO_3$ hydrate, also referred to as MgTube®) and a cross-linked polymethylmethacrylate polymer (TECHPOLYMER). The microtubular basic magnesium carbonate material comprises microtubular particles with a porous shell. The particles have an outer diameter of from about 2-10 microns, and an inner diameter of from about 1-5 microns, and a length of from about 10-50 microns. The microtubules have a pore volume of from about 7-12 mL/g. The silica and $Mg(OH)_2MgCO_3$ microparticles required surface modification to provide a hydrophobic surface since the microparticles in unmodified form are hydrophilic. The $Mg(OH)_2MgCO_3$ microtubular surface was hydrophobically modified by coating the microtubules with lauric (dodecanoic) acid. The silica was modified by reaction with the silane reagent, ODS. The polymethylmethacrylate microparticles are hydrophobic, and thus did not require additional surface modification.

The materials described in this Example that are not commercially available were made according to the following processes.

Sample 021014A (ODS-modified silica) was produced as follows. 18.0 g of hydrophilic mesoporous granulated colloidal silicon dioxide (Evonik Industries AG, Essen, Germany, part number AEROPERL 300 PHARMA) was mixed with 9.6 g of trichloro(octadecyl)silane (Sigma-Aldrich, St. Louis, Mo.) and 55 g of toluene (Sigma-Aldrich, St. Louis, Mo.). The mixture was heated at 98° C. for 2 hours at 20 mbar using a rotary evaporator (Buchi Labortechnik AG, Flawil, Switzerland, model 190) to remove the toluene from the mixture and to complete the silane coupling reaction. The powder was cooled, then rinsed with ethanol, and finally rinsed with hexane. The powder was then dried at 80° C. in vacuum to remove entrapped hexane and ethanol. Log D was then measured as described supra and the results are reported in Table 4.

Sample 021414B (Lauric acid-modified $Mg(OH)_2MgCO_3$ microtubules) was produced according to the following process. 0.5 g of $Mg(OH)_2MgCO_3$ (Nittetsu Mining Co., Tokyo, Japan), 0.25 g of lauric acid (Sigma-Aldrich, St. Louis, Mo.) and ethanol (Sigma-Aldrich, St. Louis, Mo.) were mixed and heated at 70° C. for 30 minutes. Ethanol was removed at 80° C. in vacuum at 30 mbar. Log D was then measured as described supra and the results are reported in Table 4.

Example 6

Comparison of Solid, Porous Microcarriers Associated with an Active Agent: Log D Measurements A set of experiments was performed to compare the hydrophobicity of several different types of solid, porous microcarriers that are mixed with an active ingredient, minocycline, according to processes described herein, to form a test material comprising a plurality of microcarriers and an active ingredient. The values for Log D in each case were measured according to the method described in Example 5. The results of these experiments are summarized in Table 5.

These values provide an indication of the effectiveness of partitioning the minocycline and microcarrier unit within the heptane phase. These values are approximations since the minocycline may separate from the microcarriers in the presence of water. This is particularly true for samples that have strongly negative Log D values.

TABLE 5

Measurement of Log D for a plurality of microcarriers of different types each containing a hydrophilic active ingredient. Values in parentheses indicate the percentage of the test material mass from the subject component.

| Sample # | Active ingredient | Carrier material | Overcoat | Log D | pH |
|---|---|---|---|---|---|
| 032014A | Minocycline (9.3%) | Hydrophilic silica | polyolefin wax | 1.2 | 6.7 |
| 032014B | Minocycline (9.8%) | Hydrophilic silica | magnesium stearate (50.0%) | 0.5 | 6.7 |
| 032014C | Minocycline (33.2%) | ODS-modified silica (66.8%) | None | 1.3 | 6.6 |
| 032014D | Minocycline (16.3%) | ODS-modified silica (32.2%) | polyolefin wax (51.5%) | 1.5 | 6.5 |
| 032014F | Minocycline (9.8%) | Anion exchange resin (91.1%) | None | −2.4 | 6.4 |
| 032014G | Minocycline (4.9%) | Anion exchange resin surface-modified with lauric acid (48.7%) | None | 0.0 | 6.4 |

The materials described in this Example that are not commercially available were made according to the following processes.

032014A: Hydrophilic silica with minocycline was produced according to the following process. 0.5 g of minocycline (Hovione, Loures, Portugal) was dissolved with 10 g of tetrahydrofuran (Sigma-Aldrich, St. Louis, Mo.), followed by addition of 2.3 g of silica microparticles (Evonik Industries AG, Essen, Germany, part number AEROPERL 300 PHARMA) to the mixture. Tetrahydrofuran was removed from the mixture at 45° C. under vacuum at 7 mbar. From the resulting material, 0.2 g was suspended in 2.0 g of hexane (Sigma-Aldrich, St. Louis, Mo.) with 0.21 g of polyolefin wax, (New Phase Technologies, TX, Sugar Land, product name PERFORMA V260). Hexane was removed from the mixture by heating the mixture at 45° C. in vacuum at 10 mbar. The resulting structures of microparticles and associated minocycline had an overcoat of wax with a hydrophobic surface. Log D was then measured as described supra and the results are reported in Table 5.

032014B: Hydrophilic silica with minocycline was produced according to the following process. 0.5 g of minocycline (Hovione, Loures, Portugal) was dissolved with 10 g of tetrahydrofuran (Sigma-Aldrich, St. Louis, Mo.). 2.3 g of silica microparticles (Evonik Industries AG, Essen, Germany, part number AEROPERL 300 PHARMA) were added to the mixture. Tetrahydrofuran was removed from the mixture at 45° C. and 7 mbar. From the resulting material, 0.2 g was suspended in 2.0 g of (hexane Sigma-Aldrich, St. Louis, Mo.) and under vacuum at 7 mbar. From the resulting material, 0.2 g was suspended in a mixture of 2.0 g of heptane (Sigma-Aldrich, St. Louis, Mo.) and 0.21 g of magnesium stearate (Spectrum Chemical Mfg. Corp., New Brunswick, N.J.), and the resulting mixture was heated at 80° C. to facilitate the coating of the surface of the microparticles with magnesium stearate. Heptane was removed from the mixture at 90° C. in vacuum at 10 mbar. The resulting structures of microparticles and associated minocycline had an overcoat of magnesium stearate with a hydrophobic surface. Log D was then measured as described supra and the results are reported in Table 5.

032014C ODS-modified silica was produced according to the following process. 18.0 g of hydrophilic mesoporous granulated colloidal silicon dioxide (Evonik Industries AG, Essen, Germany, part number AEROPERL 300 PHARMA) was mixed with 9.6 g of trichloro(octadecyl)silane (Sigma-Aldrich, St. Louis, Mo.) and 55 g of toluene (Sigma-Aldrich, St. Louis, Mo.). The mixture was heated at 98° C. for 2 hours at 20 mbar using a rotary evaporator (Buchi Labortechnik AG, Flawil, Switzerland, model 190) to remove the toluene from the mixture and to complete the silane coupling reactions. The powder was cooled, then rinsed with ethanol, and finally rinsed with hexane. The powder was then dried at 80° C. in vacuum to remove entrapped hexane and ethanol. From the resultant ODS-modified silica, 2.0 g was mixed with 1.0 g of minocycline (Hovione, Loures, Portugal) and 120 g of ethanol (Sigma-Aldrich, St. Louis, Mo.) at 50° C. Ethanol was removed from the mixture at 50° C. in vacuum at 10 mbar. Log D for the resultant material was then measured as described supra and the results are reported in Table 5.

032014D Wax-coated OSD-modified silica with minocycline was prepared from the material final material produced in example 032014C. The material from example 032014C was mixed with the solution of 2.0 g of hexane and 0.2 g of polyolefin wax (New Phase Technologies, Sugar Land, Tex., product name PERFORMA V260). Hexane was removed from the mixture at 45° C. in vacuum at 10 mbar. Log D was then measured as described supra and the results are reported in Table 5.

032014F Anion exchange resin with minocycline was prepared from 2.0 g of Duolite AP143/1083, cholestyramine resin, USP, (The Dow Chemical Company, Pittsburgh, Calif.) and 0.196 g of minocycline (Hovione, Loures, Portugal). Minocycline was dissolved in 17.0 g of ethanol. Then Duolite AP143/1083 was added to the minocycline solution. Ethanol was removed from the mixture at 70° C. in vacuum at 10 mbar. Log D was then measured as described supra and the results are reported in Table 5.

032014G Lauric acid-coated anion exchange resin with minocycline was prepared from the material produced in the example 032014F. Lauric acid, 0.104 g, was dissolved in 2.0 ml of hexane (Sigma-Aldrich, St. Louis, Mo.). This lauric acid solution was mixed with 0.1095 g of the anion exchange resin with minocycline from example 032014F. Hexane was removed at 65° C. in vacuum at 10 mbar. Log D was then measured as described supra and the results are reported in Table 5.

Example 7

Comparison of Solid, Porous Microcarriers Having a Hydrophobic Surface to Partition a Hydrophilic Active Agent The ability of a plurality of solid, porous microcarriers, each with a hydrophobic surface to partition a hydrophilic active ingredient into the oil phase of an oil-water mixture was demonstrated using several different materials and concentrations the active ingredient. For these experiments, the active ingredient was minocycline and the microcarriers were composed primarily of silica. In some of the experiments, the silica microcarriers were hydrophobically modified, while in some experiments the silica microcarriers were individually coated with a thin wax overcoat layer following mixing of the active ingredient with the plurality of microcarriers.

Each test material consisted of a dried mixture consisting essentially of a plurality of microcarriers and an active ingredient. The testing protocol was as follows: 1) 20 mg of the test material was mixed with 0.8 mL of cyclopentasiloxane in a 2 mL test tube in a vortex mixer at maximum speed. 2) 0.8 mL of water was added to the test tube and mixed by the vortex mixer for 2 seconds at maximum speed. 3) The mixture was held stationary for approximately 3 minutes to allow the separation of the cyclopentasiloxane and water phases. 4) 0.1 mL of each phase was transferred to a new tube and mixed with 0.9 mL of ethanol to extract any active ingredient in that phase. 5) The concentration of the active ingredient was determined by UV absorption using a wavelength of 340 nm and a UV-VIS spectrophotometer (Agilent Technologies, Santa Clara, Calif., model 8453). For these measurements, the partitioning index is defined as $Log_{10}(X_{cyclopentasiloxane}/X_{water})$, where $X_{cyclopentasiloxane}$ and $X_{water}$ are the concentration of the active ingredient in the extracted cyclopentasiloxane and water phases, respectively.

TABLE 6

Measurement of the partitioning index for a hydrophilic active ingredient in the oil phase of a cyclopentasiloxane-water mixture. Values in parentheses indicate the percentage of the test material mass from that component.

| Sample # | Active Ingredient | Plurality of microcarriers | Overcoat | Partitioning index |
|---|---|---|---|---|
| 032614M | Minocycline (100%) | None | None | −0.5 |
| 060313A | Minocycline (33.3%) | hydrophilic silica (66.7%) | None | −1.0 |
| 032614B | Minocycline (10.0%) | hydrophilic silica (90.0%) | None | −1.2 |
| 032014C | Minocycline (33.3%) | ODS-modified silica (66.7%) | None | 0.6 |
| 032614A | Minocycline (10.0%) | ODS-modified silica (90.0%) | None | 0.6 |
| 032014A | Minocycline (16.7%) | ODS-modified silica (33.3%) | polyolefin wax (50.0%) | 1.2 |

The results of these measurements are shown in Table 6. Comparing the different rows of this table allows one skilled in the art to determine factors that contribute to the retention of the active ingredient within the oil phase of the oil-water mixture.

Comparing samples with different concentrations of active ingredient (e.g., comparing the results from samples 060313A and 032614B or samples 032014C and 032614A) showed only small changes in partitioning index for this example. In other examples, the changes were more significant. One can similarly test alternate types of microcarriers in this manner to determine whether there is a notable benefit in selecting one particular concentration of the active ingredient and the degree of relevance, if any, of the concentration of active agent to the performance of the material.

Modifying the surface of the silica microcarriers had a significant effect as indicated by a difference in the partitioning index of more than 1.5 for the test material; a ratio of minocycline mass to microcarrier mass of 1:2 can be seen by comparing the results for samples 060313A and 032014C. For samples 060313A, approximately 10% of the minocycline was partitioned in the cyclopentasiloxane phase in comparison to approximately 80% for sample 032014C. Adding an overcoat of low density polyethylene wax to the microcarrier after embedding the minocycline increased the partitioning index by an additional 0.6, such that approximately 94% of the minocycline was partitioned in the cyclopentasiloxane phase.

Example 8

Preparation of Dosage Forms Having an Overcoat

Complete dosage forms were produced that demonstrated the protective boundary layer (i.e., overcoat). This overcoat separated the hydrophobic phase and the hydrophilic continuous phase of the emulsion, thus further limiting interaction between the active ingredient and the hydrophilic phase of the formulation.

Figure 5A:
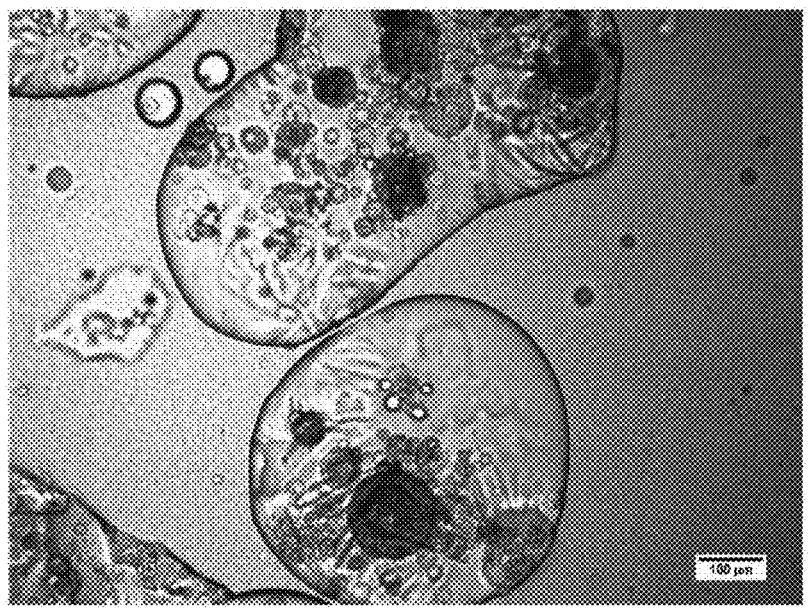
FIGS. 5A and 5B are microscope images of exemplary dosage forms produced according to Example 8. The images in FIGS. 5A and 5B were captured under white light illumination.

A representative portion of sample 120213B is shown in FIG. 5A. This sample was produced according to the following process: A minocycline and ODS-modified silica mixture was prepared for sample 032014C as described in Example 6, described supra. Then, 0.02 g of this mixture was mixed with 0.2 g mineral oil (Sigma-Aldrich, St. Louis, Mo.). Then 10 μl of ethyl 2-cyanoacrylate (Sigma-Aldrich, St. Louis, Mo.) was added. The resulting mixture was emulsified with an aqueous gel consisting of 0.7% polycarbophil (The Lubrizol Corporation, Walnut Creek, Calif.), 49.3% propylene glycol, (Spectrum Chemical Mfg. Corp., New Brunswick, N.J.), and 50% water. The introduction of the mixture into the aqueous gel caused the immediate polymerization of the ethyl 2-cyanoacrylate to form an overcoat around the hydrophobic phase. The formation of additional wall was confirmed visually under microscope.

As shown in FIG. 5A, the resulting hydrophobic phase encapsulated the plurality of microparticles which in turn were associated with the active ingredient. The ethyl 2-cyanoacrylate monomer reacted to the nucleophiles (e.g. water) in the continuous phase and formed a polymer layer at the interface between the hydrophobic phase and the continuous hydrophilic phase of the emulsion. The dimpling that was visible in the polymer wall indicated that the surface of the hydrophobic micelle was a hard shell.

Figure 5B:
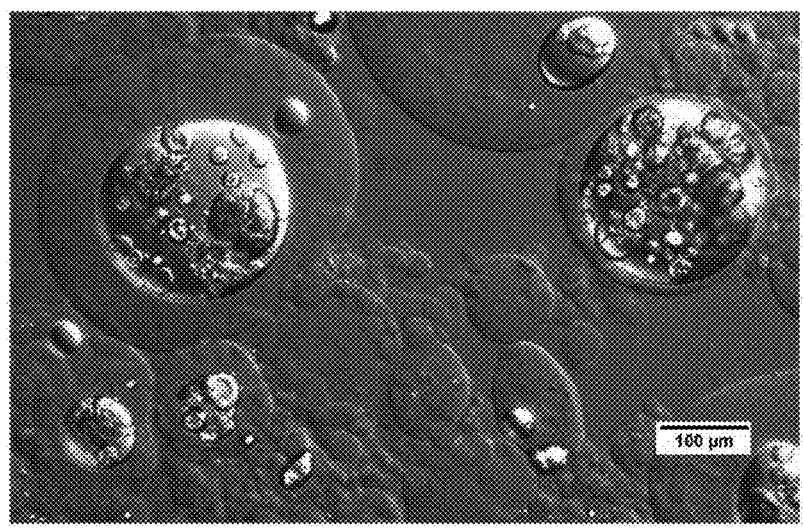

A representative portion of sample 032714A is shown in FIG. 5B. This sample was produced according to the following gelatin-polyvinylalcohol coacervation process: A minocycline and ODS-modified silica mixture was prepared for sample 032014C as described in Example 6, described supra. Then, 30 mg of this mixture was mixed with 0.15 g cyclopentasiloxane. Then, 0.15 g of the resulting mixture was emulsified at 45° C. in an aqueous gel consisting of 90% water, 5% porcine skin gelatin (Sigma-Aldrich, St. Louis, Mo., part number G2500), and 5% polyvinyl alcohol (Spectrum Chemical Mfg, Corp., New Brunswick, N.J.). The emulsion mixture was cooled to room temperature and left to rest for 1 hour. Glutaraldehyde (Sigma-Aldrich, St. Louis, Mo.) was added such that the final concentration glutaraldehyde was 0.5%. The resulting mixture was incubated for 30 minutes at 25° C. The mixture was rinsed with water and the resulting particles were separated from the wash using a centrifuge. The particles were re-suspended in 3 mL of water.

The resulting dosage form was observed by optical microscopy as shown in FIG. 5B. As shown in FIG. 5B, the resulting hydrophobic phase encapsulated the plurality of microparticles which in turn were associated with the active ingredient. The micelles (hydrophobic phase) were surrounded by a gelatin overcoat.

The invention claimed is:

1. A dosage form, comprising
   a hydrophilic active ingredient,
   a plurality of solid, porous microcarriers, each comprised of a hydrophilic material and having a hydrophobic outer surface comprising a C1-C22 hydrocarbon covalently attached thereto,
   a hydrophobic encapsulant, and
   a hydrophilic delivery agent, wherein
   (i) the hydrophilic active ingredient is associated with the plurality of solid porous microcarriers,
   (ii) the plurality of solid, porous microcarriers is encapsulated by the hydrophobic encapsulant and dispersed in the hydrophilic delivery agent,
   (iii) the associated active ingredient is partitioned from the hydrophilic delivery agent by a phase boundary between the hydrophobic encapsulant and the hydrophilic delivery agent, and
   (iv) one or more microcarriers in the plurality of solid, porous microcarriers has a minimum cross-sectional dimension in the range of about 1 micrometer to about 200 micrometers.

2. The dosage form of claim 1, wherein the Log D value of the solid, porous microcarriers is higher than the Log D value of the hydrophobic encapsulant.

3. The dosage form of claim 1, wherein the hydrophobic encapsulant comprises a material selected from the group consisting of mineral oil, petrolatum jelly, synthetic waxes, natural waxes, and silicone oils.

4. The dosage form of claim 1, wherein each of the porous microcarriers is composed of a hydrophilic material selected from the group consisting of silicon dioxide, metal oxides, zeolites, porous polyamide, metal salts, porous cellulose, and porous polytetrafluoroethylene.

5. The dosage form of claim 1, wherein the dosage form is for topical use.

6. The dosage form of claim 5, wherein the dosage form is for topical application to human skin.

7. The dosage form of claim 1, wherein the hydrophilic active ingredient comprises a small molecule drug having a molecular weight of less than about 1000.

8. The dosage form of claim 7, wherein the small molecule drug is an antibiotic.

9. The dosage form of claim 8, wherein the antibiotic is a tetracycline-class antibiotic.

10. The dosage form of claim 9, wherein the tetracycline-class antibiotic is minocycline or a derivative of minocycline.

11. The dosage form of claim 10, wherein the dosage form is indicated for the treatment of acne.

12. The dosage form of claim 1, wherein the dosage form is indicated for the treatment of acne.

13. The dosage form of claim 1, wherein the dosage form is a dietary supplement.

14. The dosage form of claim 13, wherein the active ingredient is selected from the group consisting of L-methylfolate, vitamin C, and choline hydroxide.

15. The dosage form of claim 5, wherein the dosage form is a cosmetic and the active ingredient comprises one or more substances effective to bring about a measurable change in one or more cosmetic skin parameters.

16. The dosage form of claim 1, wherein the dosage form is a solid or semi-solid.

17. The dosage form of claim 1, wherein the dosage form is a liquid.

18. The dosage form of claim 1, wherein one or more microcarriers in the plurality of solid, porous microcarriers has a minimum cross-sectional dimension in the range of about 5 micrometers to about 50 micrometers.

19. The dosage form of claim 1, further comprising an emulsifier.

20. The dosage form of claim 1, wherein the C1-C22 hydrocarbon is selected from the group consisting of C-1, C-2, C-3, C-4, C-5, C-6, C-7, C-8, C-9, C-10, C-11, C-12, C-13, C-14, C-15, C-16, C-17, C-18, C-19, and C-20 hydrocarbons.

* * * * *